(12) United States Patent
Kolb et al.

(10) Patent No.: US 8,293,206 B2
(45) Date of Patent: Oct. 23, 2012

(54) ACHIEVEMENT OF A HIGH THERAPEUTIC INDEX THROUGH MOLECULAR IMAGING GUIDED TARGETED DRUG TREATMENT

(75) Inventors: Hartmuth C. Kolb, Playa Del Rey, CA (US); Joseph C. Walsh, Pacific Palisades, CA (US); Kai Chen, Rockville, MD (US); Dhanalakshmi Kasi, Los Angeles, CA (US); Umesh B. Gangadharmath, Los Angeles, CA (US); Peter J. H. Scott, Ypsilanti, MI (US); Gang Chen, Los Angeles, CA (US); Vani P. Mocharla, Los Angeles, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 516 days.

(21) Appl. No.: 12/455,346

(22) Filed: Jun. 1, 2009

(65) Prior Publication Data
US 2010/0074910 A1 Mar. 25, 2010

Related U.S. Application Data

(60) Provisional application No. 61/057,774, filed on May 30, 2008.

(51) Int. Cl.
*A61M 36/14* (2006.01)
*A61K 39/00* (2006.01)
(52) U.S. Cl. .................... 424/1.69; 424/181.1
(58) Field of Classification Search .............. 424/1.69, 424/181.1
See application file for complete search history.

(56) References Cited

U.S. PATENT DOCUMENTS

| 6,534,478 | B1 | 3/2003 | Jonczyk et al. |
| 6,537,520 | B1 | 3/2003 | Rajopadhye et al. |
| 7,666,392 | B2 | 2/2010 | Kolb et al. |
| 2003/0125243 | A1 | 7/2003 | Liu et al. |
| 2009/0074664 | A1 | 3/2009 | Kolb et al. |

FOREIGN PATENT DOCUMENTS

| WO | 9901472 A1 | 1/1999 |
| WO | WO 2006135233 A1 | 12/2006 |
| WO | WO 2007/018431 | * 2/2007 |
| WO | WO 2007018431 A2 | 2/2007 |
| WO | WO 2008033557 A2 | 3/2008 |
| WO | WO 2008033561 A2 | 3/2008 |

OTHER PUBLICATIONS

Dijkgraaf et al. Org. Biomol. Chem., 2007, 5, 935-944 (in IDS: Feb. 9, 2010).*
West et al. Current Drug Discovery Technologies, 2005, 2, 123-160.*
Schmidt, et al. "Synthesis of Entantriomerically Pure and Compatibly Protected (2S, 3R)- and (2S, 3S)-Diaminobutyric Acids" Published in Synthesis, No. 12, 1992 (pp. 1201-1202); Magazine.
Kuijpers, et al. "Expedient synthesis of triazole-linked glycosyl amino acids and peptides" Published by Organic Letters, American Chemical Society, vol. 6, No. 18, Sep. 2, 2004 (pp. 3123-3126); Magazine.
Oppolzer, et al. "Non-destructive Cleavage of N-Acylsultams Under Neutral Conditions: Preparation of Enantiomerically Pure Fmoc-Protected alpha-Amino Acids" Published by Helvetica Chimica Acta, vol. 75, 1992 (pp. 2572-2582); Magazine.
Franke, et al. "Peptide ligation through click chemistry for the generation of assembled and scaffolded peptides" Published in Tetrahedron Letters, Elsevier, Science Direct, vol. 46, No. 26, Jun. 27, 2005 (pp. 4479-4482); Magazine.
International Search Report in Application No. PCT/US2009/003309 dated Nov. 12, 2009.
Cai, et al., "A thiol-reactive F-labeling agent N[2-(4-18F-Flurobenzamido) Ethyl] Maleimide, and synthesis of RGD peptide-based tracer for PET imaging of alpha v beta 3 integrin expression", Journal of Nuclear Medicine, Society of Nuclear Medicine, Reston, VA, US, vol. 47, No. 7, Jul. 1, 2006; pp. 1172-1180.
Wu, et al., "MicroPET Imaging of Glioma Integrin (alpha)v(beta)3 Expression Using 64Cu-Labeled Tetrameric RGD Peptide", Published in Journal of Nuclear Medicine: Official Publication, Society of Nuclear Medicine Oct. 2005, vol. 46, No. 10 (pp. 1707-1718).
Goodman, et al., "Nanomolar Small Molecule Inhibitors for Alphavbeta6, Alphavbeta5, Integrins", Journal of Medicinal Chemistry, American Chemical Society, Washington, US, vol. 45, Jan. 31, 2002 (pp. 1045-1051).
Preliminary Report on Examination for Application No. PCT/US2008/071266 dated Nov. 25, 2009.
Haubner, et al.: "(18F) Galacto-RGD: Synthesis, Radiolabeling, Metabolic Stability, and Radiation Dose Estimates" Bioconjugate Chemistry, ACS, Washington, DC, US, vol. 15, No. 1, Jan. 1, 2004, pp. 61-69, only the first page.
Chen, et al.: "MicroPET Imaging of brain tumor angiogenesis with 18 F labeled PEGylated RGD peptide", European Journal of Nuclear Medicine and Molecular Imaging, Springer Verlag, Heidelberg, DE, vol. 31, No. 8, Aug. 1, 2004, only the first page.
Chen, et al.: "Pegylated Arg-Gly-Asp Peptide: 64 Cu Labeling and PET Imaging of Brain Tumor alphabeta3-integrin expression", Journal of Nuclear Medicine, Society of Nuclear Medicine, Reston VA, US, vol. 45, No. 10, Oct. 2004, pp. 1776-1783, only the first page.
Belvisi et al.: "Potent Integrin Antagonists From a Small Library of RGD-including Cyclic Pseudopeptides", Organic Letters, vol. 3, No. 7, 2001, pp. 1001-1004, only the first page.
Ryppa Claudia et al.: "In vitro and in vivo evalution of doxorubicin conjugates with the divalent peptide E-[c(RGDfK)(2)] that targets integrin alpha(v)beta(3)" Bioconjugate Chemistry, vol. 19, No. 7, Jul. 2008, pp. 1414-1422; XP002538414; ISSN: 1043-1802; Magazine; 2008; US.

(Continued)

*Primary Examiner* — Ileana Popa
*Assistant Examiner* — Genevieve S Alley
(74) *Attorney, Agent, or Firm* — Joshua Ryan

(57) ABSTRACT

The present disclosure provides methods for treating cancer in a patient in need of such treatment, the method includes prequalifying a patient's therapeutic treatment by performing a molecular imaging procedure to the patient using a labeled biomarker specific for a cancer target at the tumor site; and administering a therapeutic effective amount of a compound comprising a targeting agent linked to a chemotherapeutic or a targeting agent linked to an antibody. Embodiments of the present invention also include compounds and compositions for using such methods.

30 Claims, 7 Drawing Sheets

OTHER PUBLICATIONS

Dijkgraaf Ingrid et al.: "Synthesis of DOTA-conjugated multivalent cyclic-RGD peptide dendrimers via 1, 3-dipolar cycloaddition and their biological evaluation: implications for tumor targeting and tumor imaging purposes" Organic and Biomolecular Chemistry, Royal Society of Chemistry, Cambridge, GB, vol. 5, No. 6, Mar. 21, 2007; pp. 935-944, XP002470091; ISSN: 1477-0520; Magazine; 2007; GB.

Li Zi-Bo et al.: "Click chemistry for (18)F-labeling of RGD peptides and microPET imaging of tumor integrin alphavbeta3 expressin" Bioconjugate Chemistry, ACS, Washington, DC, US; vol. 18, No. 6; Nov. 1, 2007, pp. 1987-1994, XP002470093; ISSN: 1043-1802; Magazine; 2007; US.

Jeong Jae Min et al.: "Preparation of a promising angiogenesis PET imaging agent: Ga-68-labeled c(RGDyK)-isothicoyanatobenzyl-1, 4, 7-triaza cyclononane-1, 4, 7-triacetic acid and feasibility studies in mice" Journal of Nuclear Medicine, vol. 49, No. 5, May 2008; pp. 830-836, XP002538417; ISSN: 0161-5505; Magazine; 208; US.

Hamidpour Mohsen et al.: "The isolation and characterization of antiplatelet antibodies" European Journal of Haematology, vol. 76, No. 4, Apr. 2006; pp. 331-338; XP002538413; Magazine; 2006; GB.

International Search Report for Application No. PCT/US2009/002627 dated Nov. 17, 2009.

International Search Report for Application No. PCT/US2008/059599 dated Dec. 3, 2008.

Haubner, et al.: "(18F] Galacto-RGD: Synthesis, Radiolabeling, Metabolic Stability, and Radiation Dose Estimates" Bioconjugate Chemistry, ACS, Washington, DC, US, vol. 15, No. 1, Jan. 1, 2004, pp. 61-69.

Chen, et al.: "MicroPET Imaging of brain tumor angiogenesis with 18 F labeled PEGylated RGD peptide", European Journal of Nuclear Medicine and Molecular Imaging, Springer Verlag, Heidelberg, DE, vol. 31, No. 8, Aug. 1, 2004.

Chen, et al.: "Pegylated Arg-Gly-Asp Peptide: 64 Cu Labeling and PET Imaging of Brain Tumor alphabeta3-integrin expression", Journal of Nuclear Medicine, Society of Nuclear Medicine, Reston VA, US, vol. 45, No. 10, Oct. 2004, pp. 1776-1783.

Belvisi et al.: "Potent Integrin Antagonists From a Small Library of RGD-including Cyclic Pseudopeptides", Organic Letters, vol. 3, No. 7, 2001, pp. 1001-1004.

* cited by examiner

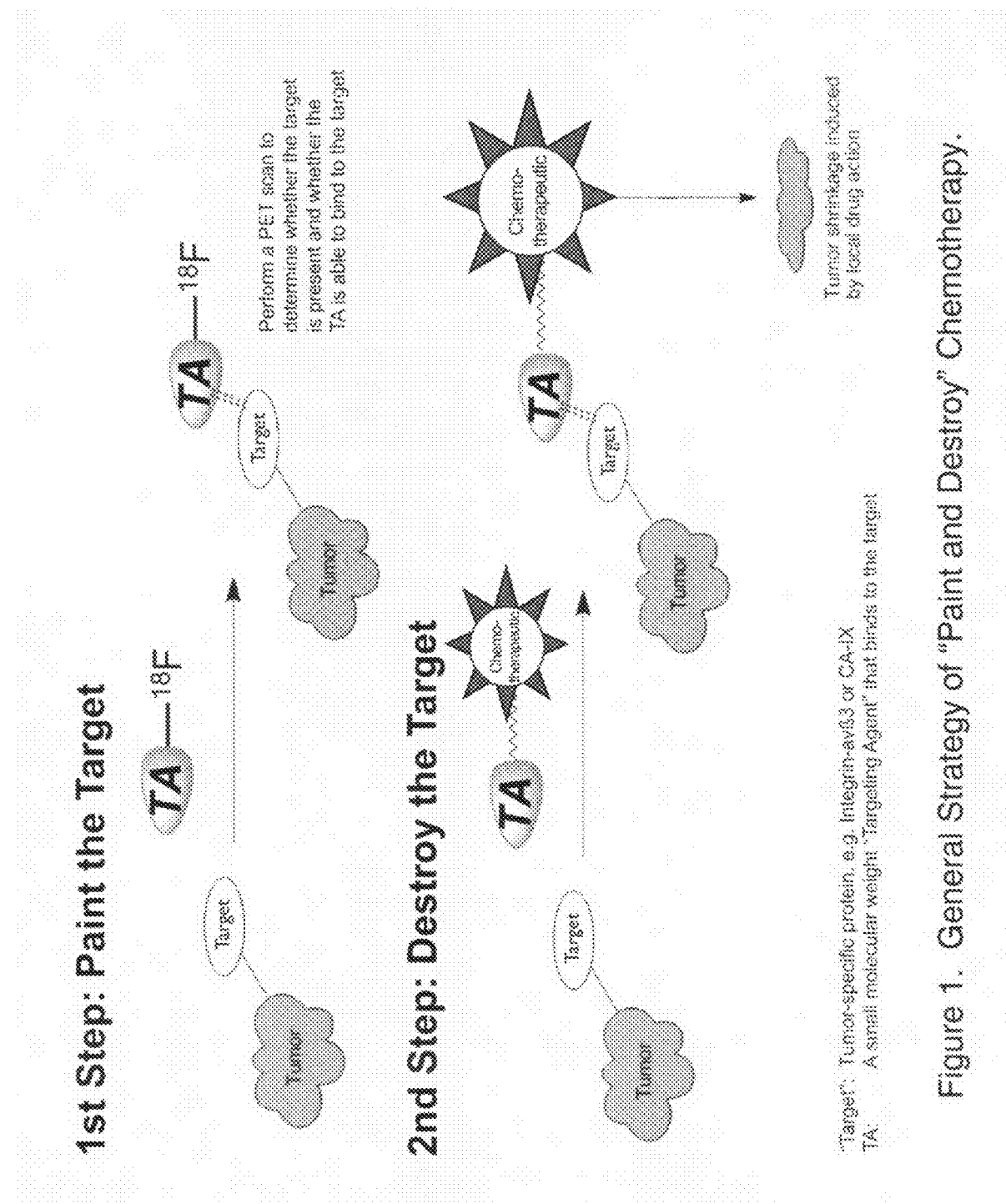
Figure 1. General Strategy of "Paint and Destroy" Chemotherapy.

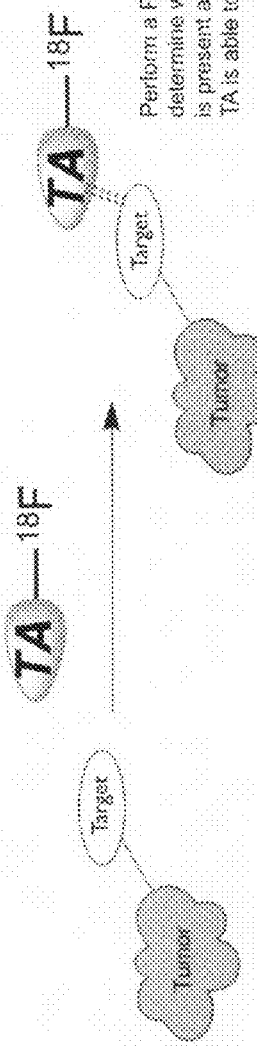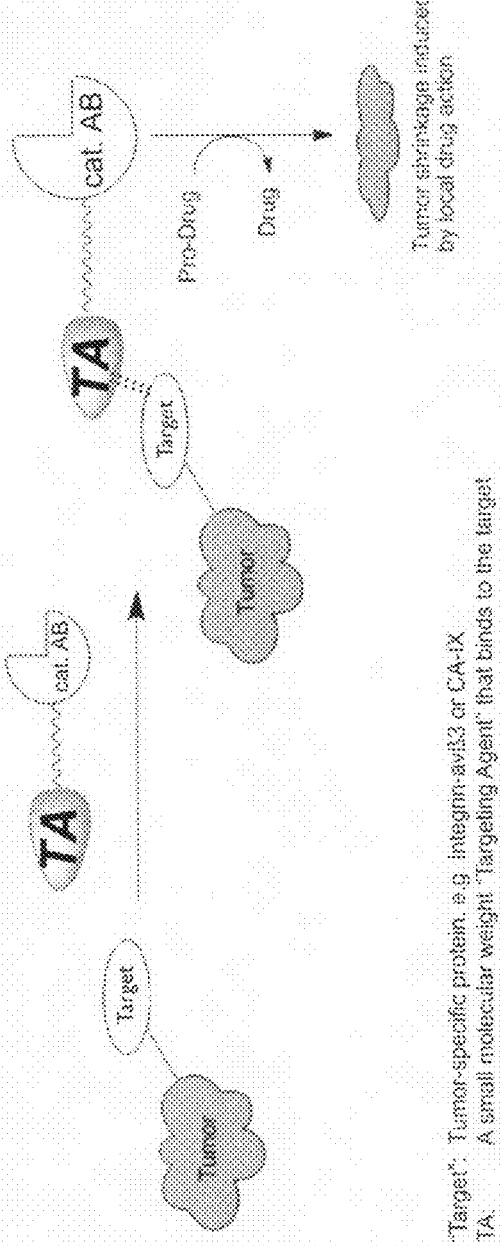
Figure 2. General Strategy of "Paint and Destroy" Chemotherapy Using Antibodies.

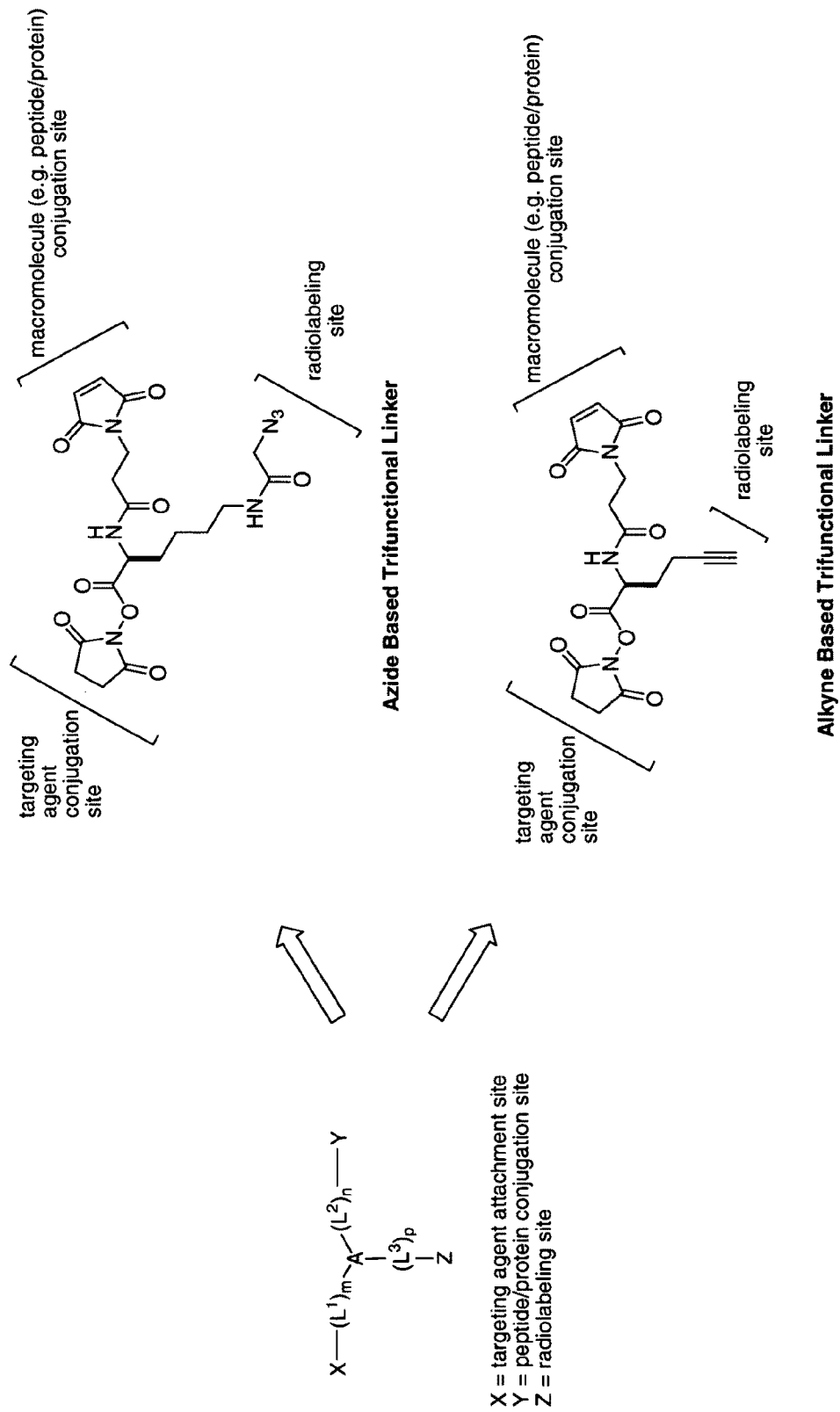
Figure 3. Exemplary Trifunctional Linkers for Polyfunctional Paint and Destroy Conjugates.

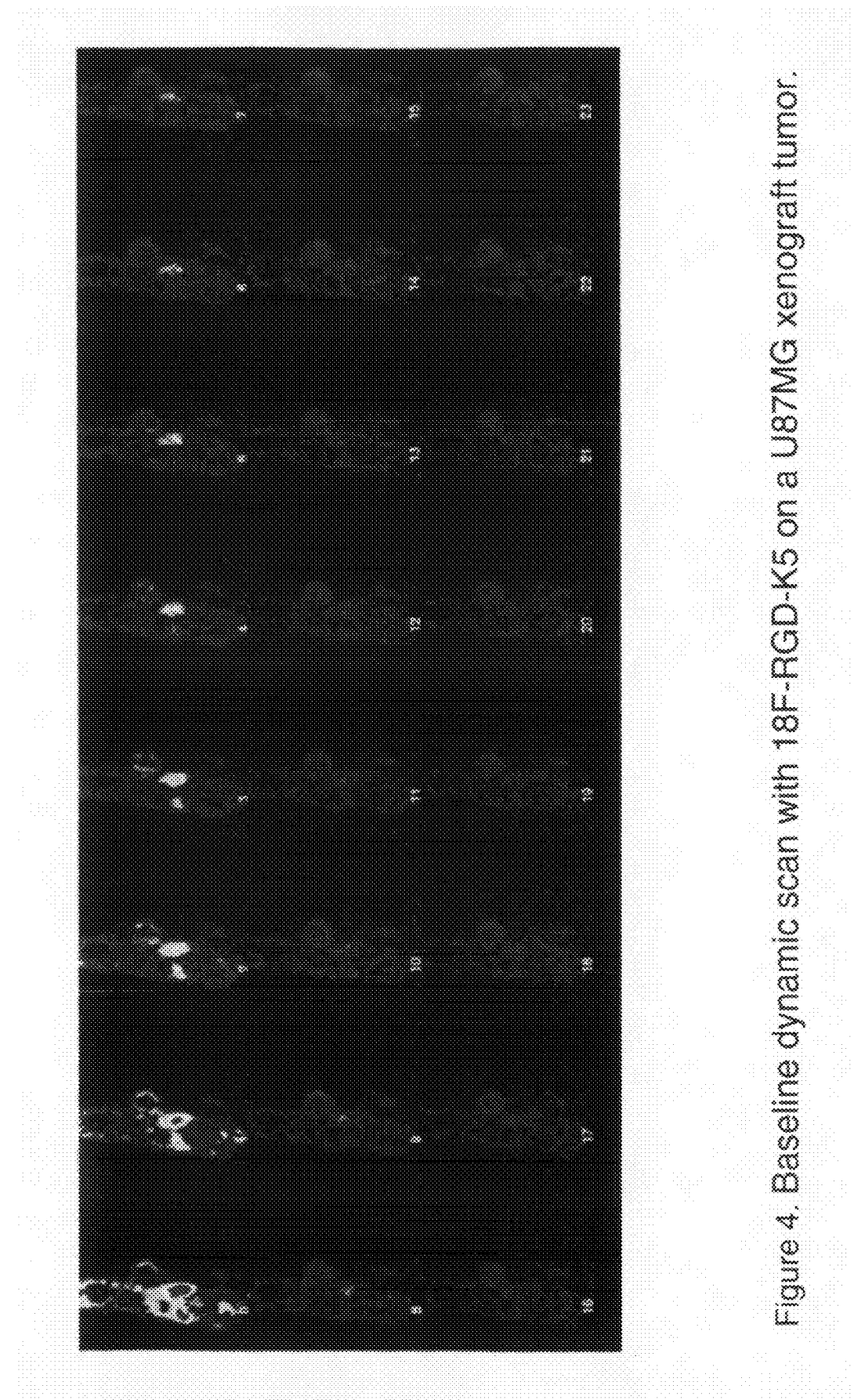
Figure 4. Baseline dynamic scan with 18F-RGD-K5 on a U87MG xenograft tumor.

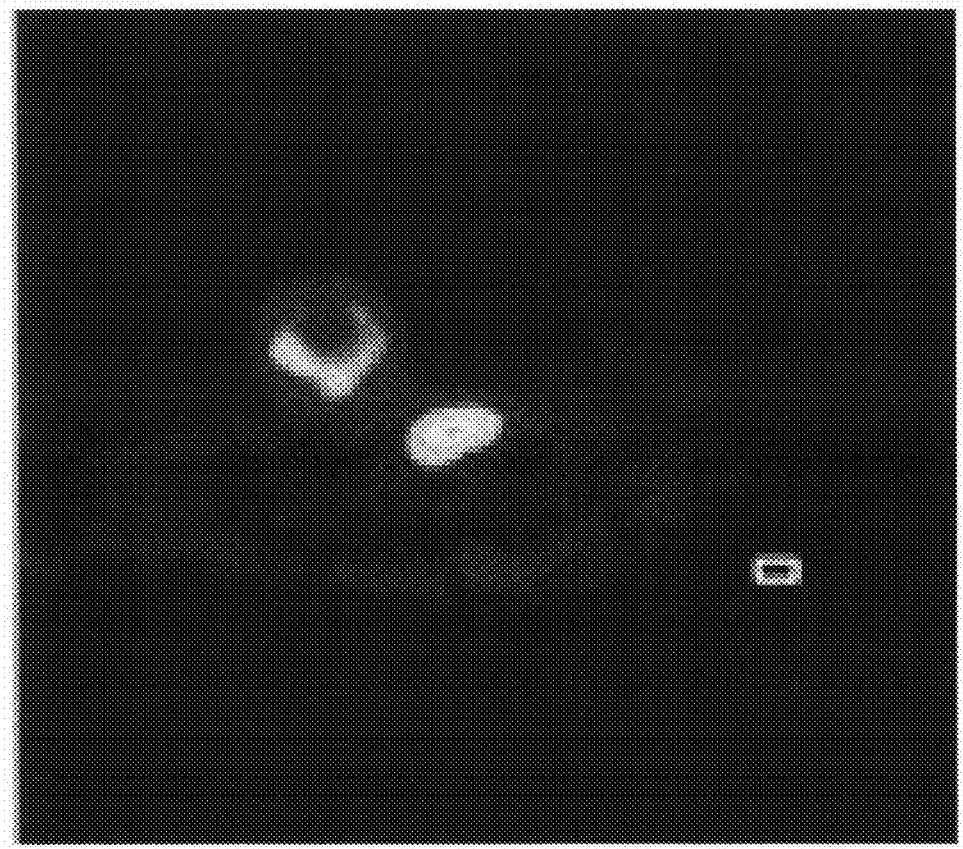
Figure 5. Static scan with 18F-RGD-K5 on a BXPC3 xenograft tumor.

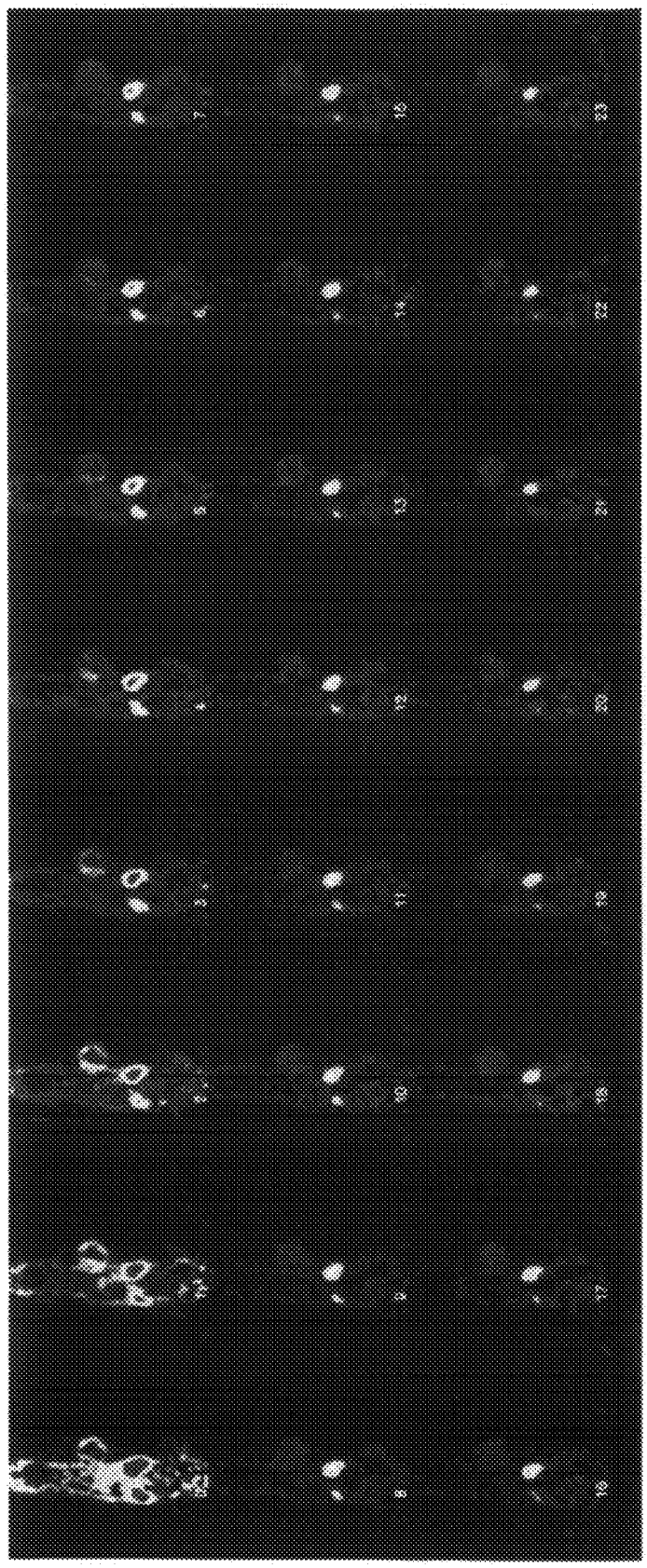
Figure 6. Baseline dynamic scan with 18F-42 on a U87MG xenograft tumor.

Figure 7. Static scan with 18F-42 on a BXPC3 xenograft tumor.

ACHIEVEMENT OF A HIGH THERAPEUTIC INDEX THROUGH MOLECULAR IMAGING GUIDED TARGETED DRUG TREATMENT

CROSS REFERENCE TO RELATED APPLICATIONS

This application claims benefit of U.S. provisional patent application Ser. No. 61/057,774 filed May 30, 2008.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference in their entirety, and may be employed in the practice of the invention.

FIELD OF THE INVENTION

Embodiments of the present invention are directed to polyfunctional compounds comprising radiolabeled targeting agents linked to therapeutic agents, pharmaceutical compositions thereof, and methods of using polyfunctional compounds comprising radiolabeled targeting agents linked to therapeutic agents. The present invention also includes embodiments that are further directed to methods of preparing the polyfunctional compounds. Such polyfunctional compounds, as disclosed herein, may be used in imaging studies and as therapeutics for treatment of disease.

BACKGROUND OF THE INVENTION

Chemotherapeutic interventions for combating metastatic cancer are one of the most widely accepted forms of cancer therapy. Through empirical discovery, many successful chemotherapeutics were developed largely independently of their biochemical mechanism of action. Chemotherapeutic regimens have undergone various refinements as a result of extensive preclinical and clinical investigations, yet the fundamentally inherent treatment drawbacks of chemotherapeutics still exist. For example, their relatively narrow therapeutic index, coupled with systemic toxicity and low selectivity for neoplastic cells, signals a major drawback in chemotherapeutic-based patient care. In addition, chemotherapeutic regimens may not necessarily take advantage of a tumor's prevailing biochemical profile, thus leading to therapies that are not personalized for the patient, and may ultimately fail to elicit an effective outcome.

Molecular imaging helps elucidate the biochemical profile of a given tumor leading to both potentially more focused and effective treatments. Cancer patients, whose tumors respond to specific tracers, provide therapeutic clues towards treatments with the highest percentages of success. In addition, after treatment has begun, follow up imaging can help determine the efficacious nature of the therapy and can quickly guide decisions regarding the need possible for alternative therapies. For example, there exists a sub-population of cancer patients that may benefit from anti-angiogenesis or anti-carbonic anhydrase IX (CA-IX) therapy. In these circumstances, the use of very expensive antibody-based therapeutics or very toxic treatments (i.e. chemotherapies) should be qualified prior to patient treatment, and a predictive molecular imaging test would have clear health and cost benefits.

Several examples of molecular imaging or marker agents are described, for example in U.S. Ser. Nos. 11/399,294; 11/413,596; 11/673,909; 11/901,704; 11/901,730; 12/074,583; and 12/180,444.

Consequently, it would be an advancement in the art to have improved agents which provide both biochemical an biophysical feedback allowing for tailored therapy for afflictions. It would also be an advancement in the art to provide a highly localized concentration of a therapeutic agent in order to minimize peripheral side effects while retaining desired efficacy. Therefore, a continuing need exists for novel compounds and methods for the treatment of cancers.

Citation or identification of any document in this application is not an admission that such document is available as prior art to the present invention.

SUMMARY OF THE INVENTION

Diagnostic Solutions: MI Guided Targeted Cancer Therapy; "Paint the Target"

There are several beneficial outcomes of molecular imaging (MI) when used for clinical imaging purposes. For example, molecular imaging can be employed in an effort to conduct more effective clinical trials for highly specific cancer therapeutics. More specifically, the patient recruitment population would reflect those whose tumor biology matched the mechanism of action of the cancer drug. Thus, clinical trials of anti-angiogenic therapies, for example, would include only those patients whose tumors show positive uptake of $^{18}$F-angiogenesis tracers as revealed by PET imaging, indicating tumor angiogenesis.

Molecular imaging also plays a beneficial role in guiding personalized therapies. In order to determine a patient's specific treatment regimen, the patient is first imaged using biomarkers to establish the presence or absence of a specific cancer target at the tumor site (e.g. CA-IX or integrin-$\alpha v\beta 3$), thereby illuminating the decision path regarding whether a given treatment, that may be toxic or expensive, would be successful. As a specific example, angiogenic therapies would be considered a possible treatment strategy if molecular imaging revealed angiogenic factors at the tumor site.

Finally, molecular imaging is uniquely situated to monitor a patient's treatment response. Molecular imaging with an appropriate biomarker can help visualize biochemical changes as a function of both time and treatment. Clinicians, in parallel, can determine whether or not a current therapeutic regimen has elicited the desired biological effect as measured, for example, by the reduction of blood vessel growth, tumor shrinkage or cell death. This complimentary analysis approach provides both biochemical and biophysical feedback allowing for potentially more sensitive estimation of a patient's response to therapy.

Diagnostic—Therapeutic Solutions: "Paint and Destroy the Target"

After molecular imaging confirms the presence of a specific target (i.e. "paint the target") the clinician determines the most favorable treatment protocol in order to "destroy the target". Such treatment protocol may include the administration of a chemotherapeutic agent or an antibody. Positron Emission Tomography (PET) imaging with small molecule PET biomarkers are best suited for this approach, due to their very fast tracer kinetics, which allows imaging ("Painting") and initiation of treatment ("Destroying") to be performed within a few hours. There are two main variants of this approach: 1) administering a targeting agent linked to an active therapeutic and/or 2) administering a targeting agent linked to a catalytic antibody, which converts a pro-drug into an active chemotherapeutic drug. The pro-drug may be inactive, relatively inactive or may exhibit low biological activity when compared to the active chemotherapeutic drugs.

Accordingly, it is an embodiment of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 1 is a cartoon representation of the general strategy of "Paint and Destroy" chemotherapy.

FIG. 2 is a general strategy of "Paint and Destroy" chemotherapy using antibodies.

FIG. 3 is a generalized structure of trifunctional linkers for the polyfunctional "Paint and Destroy" conjugates.

FIG. 4 shows the baseline dynamic scan with $^{18}$F-RGD-K5 on a U87MG xenograft tumor.

FIG. 5 shows the static scan with $^{18}$F-RGD-K5 on a BXPC3 xenograft tumor.

FIG. 6 shows the baseline dynamic scan with $^{18}$F-42 on a U87MG xenograft tumor.

FIG. 7 shows the static scan with $^{18}$F-42 on a BXPC3 xenograft tumor.

DETAILED DESCRIPTION

The following embodiments, aspects and variations thereof are exemplary and illustrative are not intended to be limiting in scope.

In one embodiment, there is provided a method for using a targeting agent linked to a therapeutic, wherein the method comprises two stages of diagnosis followed by treatment (FIG. 1). First, a PET image is performed with a labeled agent, such as an $^{18}$F-labeled target-specific agent, "targeting agent" $^{18}$F-TA, to determine whether or not the tumor is associated or carries this target ("Paint the Target"). Such targeting agent may include an $^{18}$F-labeled tracer that targets integrin-αvβ3. If the target is present, the treatment involves administration, such as by injection, a targeting agent (TA) that is linked to a chemotherapeutic agent into the patient. Such chemotherapeutic agent may include, for example, doxorubicin, which is a cytotoxic agent, see, for example U.S. Ser. No. 11/399,294. The TA-Chemotherapeutic conjugate will preferentially bind to the tumor, resulting in a high local concentration of the therapeutic agent, and thereby treat the target (i.e, "Destroy the Target.") This highly localized concentration of the therapeutic agent increases effectiveness of the chemotherapeutic and minimizes the harmful side effects, ultimately leading to a desired high therapeutic index.

In an alternate embodiment of this approach, the PET isotope, such as $^{18}$F, may be attached directly to the TA-Chemotherapeutic conjugate, as this may also allow "real time" PET imaging to determine whether or not the $^{18}$F-labeled TA-CA conjugate does indeed bind to the tumor.

In another embodiment, there is provided a method whereby the targeting agent is linked to an antibody (FIG. 2). In this method, the similar principles may be employed, however the method of treatment varies slightly. An initial assessment of the tumor is carried out with an imaging procedure, such as PET imaging with an $^{18}$F-labeled target-specific agent, i.e., a "targeting agent" (18F-TA), to determine whether or not the tumor carries this target ("Paint the Target").

In one embodiment, the targeting agent may be an $^{18}$F-labeled tracer that targets integrin-αvβ3. If the target is present, the treatment therapy may proceed along two possible paths. First, the treatment may commence by administering a TA that is linked to a catalytic antibody, followed by the administration of a pro-drug that is selectively activated by the catalytic antibody. Because the catalytic antibody uniquely converts the inactive pro-drug into an active chemotherapeutic agent locally, there is a high local concentration of the active chemotherapeutic, which will "destroy the target", leading to increased effectiveness and minimized side effects (i.e., achieving high therapeutic index).

Alternatively, another embodiment may include the employment of the $^{18}$F-TA imaging agent wherein the agent already comprises a binding site for the catalytic antibody. This alternative embodiment may provide a more seamless method of PET imaging ("Paint") and treatment ("Destroy") protocol.

In a further embodiment, the treatment may commence by administering a targeting agent TA that is linked to an antibody AB. Antibody targeting compounds are described, for example, in U.S. Ser. No. 10/420,373. In this embodiment, the TA confers specificity of the antibody and the localization of such complexes at the tumor site are known to decrease a tumor's size (Popkov, M.; Rader, C.; Gonzalez, B.; Sinha, S.; Barbas, C. F. Int. J. Cancer 2006, 119, 1194-1207) which "destroys the target".

In yet another embodiment, the $^{18}$F-TA imaging agent may also already comprise a binding site for the catalytic antibody.

In one embodiment of the invention, there is provided a polyfunctional compound of the Formula I:

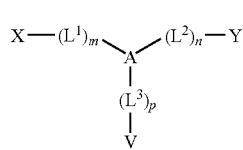

I wherein:
A is a low molecular weight scaffold selected from the group consisting of functionalized monocyclic and polycyclic hydrocarbons, functionalized monocyclic and polycyclic heterocycles, an amino acid residue, linear peptides, cyclic peptides, synthetic peptides, semisynthetic peptides, peptidomimetics and hyaluronic acid, and derivatives thereof;

each $L^1$, $L^2$ and $L^3$ is independently a bond, a linker selected from the group consisting of an amino acid residue, —O—, —S—, —S(O)—, —S(O)$_2$—, —NR$^a$—, $C_{1-6}$alkyl, and —(CH$_2$CH$_2$O)$_{1-15}$, wherein $R^a$ is H, $C_{1-5}$alkyl, heterocyclyl, aryl, or heteroaryl, and wherein 1 or 2 carbon atoms of the $C_{1-6}$alkyl are optionally replaced by a —O—, —C(O)—, —C(O)NR'—, —S—, —S(O)—, —S(O)$_2$—, —S(O)$_2$NR'— or —NR'—, wherein R' is H or $C_{1-5}$alkyl, and wherein the $C_{1-6}$alkyl is optionally substituted with 1 or 2 substituents selected from the group consisting of —OH, —SH, —NH$_2$, heterocyclyl, aryl and heteroaryl;

V is —N$_3$ or $C_2$-$C_4$alkynyl;
X is an activated moiety of a carboxyl group;
Y is electrophilic group; and
each m, n and p is independently an integer of 1 to 10; or a pharmaceutically acceptable salt thereof, optionally in the form of a single stereoisomer or mixtures of stereoisomers thereof.

In another embodiment of the invention, there is provided a polyfunctional compound of the Formula Ia:

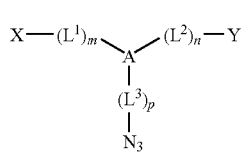

Ia wherein:
A is a low molecular weight scaffold selected from the group consisting of functionalized monocyclic and polycyclic hydrocarbons, functionalized monocyclic and polycyclic heterocycles, an amino acid residue, linear peptides, cyclic peptides, synthetic peptides, semisynthetic peptides, peptidomimetics and hyaluronic acid, and derivatives thereof;

each $L^1$, $L^2$ and $L^3$ is independently a bond, a linker selected from the group consisting of an amino acid residue, —O—, —S—, —S(O)—, —S(O)$_2$—, —NR$^a$—, $C_{1-6}$alkyl, and —(CH$_2$CH$_2$O)$_{1-15}$, wherein $R^a$ is H, $C_{1-5}$alkyl, heterocyclyl, aryl, or heteroaryl, and wherein 1 or 2 carbon atoms of the $C_{1-6}$alkyl are optionally replaced by a —O—, —C(O)—, —C(O)NR'—, —S—, —S(O)—, —S(O)$_2$—, —S(O)$_2$NR'— or —NR'—, wherein R' is H or $C_{1-5}$alkyl, and wherein the $C_{1-6}$alkyl is optionally substituted with 1 or 2 substituents selected from the group consisting of —OH, —SH, —NH$_2$, heterocyclyl, aryl and heteroaryl;

X is an activated moiety of a carboxyl group;
Y is electrophilic group; and
each m, n and p is independently an integer of 1 to 10; or a pharmaceutically acceptable salt thereof, optionally in the form of a single stereoisomer or mixtures of stereoisomers thereof.

In another embodiment of the invention, there is provided a polyfunctional compound of the Formula Ib:

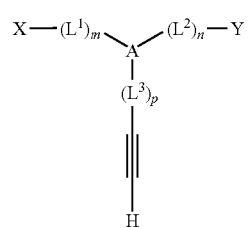

Ib wherein:
A is a low molecular weight scaffold selected from the group consisting of functionalized monocyclic and polycyclic hydrocarbons, functionalized monocyclic and polycyclic heterocycles, an amino acid residue, linear peptides, cyclic peptides, synthetic peptides, semisynthetic peptides, peptidomimetics and hyaluronic acid, and derivatives thereof;

each $L^1$, $L^2$ and $L^3$ is independently a bond, a linker selected from the group consisting of an amino acid residue, —O—, —S—, —S(O)—, —S(O)$_2$—, —NR$^a$—, $C_{1-6}$alkyl, and —(CH$_2$CH$_2$O)$_{1-15}$, wherein $R^a$ is H, $C_{1-5}$alkyl, heterocyclyl, aryl, or heteroaryl, and wherein 1 or 2 carbon atoms of the $C_{1-6}$alkyl are optionally replaced by a —O—, —C(O)—, —C(O)NR'—, —S—, —S(O)—, —S(O)$_2$—, —S(O)$_2$NR'— or —NR'—, wherein R' is H or $C_{1-5}$alkyl, and wherein the $C_{1-6}$alkyl is optionally substituted with 1 or 2 substituents selected from the group consisting of —OH, —SH, —NH$_2$, heterocyclyl, aryl and heteroaryl;

X is an activated moiety of a carboxyl group;
Y is electrophilic group; and
each m, n and p is independently an integer of 1 to 10; or a pharmaceutically acceptable salt thereof, optionally in the form of a single stereoisomer or mixtures of stereoisomers thereof.

In certain embodiments, the molecular weight fragment A of the present application is at least 10 daltons, 50 daltons, 75 daltons, 100 daltons or at least 500 daltons.

In one embodiment, the peptidomimetics or peptide mimetics, particularly the peptide portions of the peptide mimetics of the present application, may be prepared by the solid phase method using standard methods known in the art, such as, by way of non-limiting example, those based on either t-butyloxycarbonyl (BOC) or 9-fluorenylmethoxy-carbonyl (FMOC) protecting groups.

In some embodiments, the scaffold A may include hyaluronic acid derivatives, including their amides and ester derivatives. Such hyaluronic acid derivatives are described, by way of non-limiting example, in WO95/24429, the disclosure of which is incorporated herein by reference. WO95/24429 discloses highly reactive esters of carboxy polysaccharides, including hyaluronic acid, and derivatives of hyaluronic acid comprising disaccharide subunits, wherein at least one of the said disaccharide subunits is a substituted disaccharide subunit having a substitution at a carboxyl group. The hyaluronic acid derivatives or functional groups on the hyaluronic acid may be selected from the group consisting of peptides, aldehydes, amines, arylazides, hydrazides, maleimides, sulfhydryls and active esters.

In one embodiment, A is selected from the group consisting of an amino acid residue, linear peptides, cyclic peptides, synthetic peptides, semisynthetic peptides, peptidomimetics and derivatives thereof.

In another embodiment, A is an amino acid residue or a dipeptide.

In still another embodiment, A is a lysine residue.

In yet another embodiment, V is an azide;

In yet another embodiment, V is $C_2$-$C_4$alkynyl;

In yet another embodiment, V is ethynyl;

In a particular embodiment, the peptides may be comprised of natural and/or unnatural amino acids, peptide mimetics, conservative amino acid substitutions of these peptides, peptides and polypeptide homologs and combinations thereof, the preparation and use are as provided herein and also well known to one skilled in the art.

In yet another embodiment, there is provided a compound of formula (I) wherein:
 A is selected from the group consisting of an amino acid residue, linear peptides, cyclic peptides, synthetic peptides, semi synthetic peptides, peptidomimetics and derivatives thereof;
 each $L^1$, $L^2$ and $L^3$ is independently a bond or a $C_{1-6}$alkyl wherein 1 or 2 carbon atoms of the $C_{1-6}$alkyl are optionally replaced by a —O—, —C(O)—, —C(O)NR'—, —S—, —S(O)—, —S(O)$_2$—, —S(O)$_2$NR'— or —NR', wherein R' is H or $C_{1-5}$alkyl, and
 wherein the $C_{1-6}$alkyl is optionally substituted with 1 or 2 substituents selected from the group consisting of —OH, —SH, —NH$_2$, heterocyclyl, aryl and heteroaryl; and
 each m, n and p is 1.

In a particular embodiment, A is selected from the group consisting of functionalized monocyclic and polycyclic hydrocarbons, functionalized monocyclic and polycyclic heterocycles, an amino acid residue, linear peptides, cyclic peptides, synthetic peptides, semisynthetic peptides, peptidomimetics and hyaluronic acid, and derivatives thereof;
 each $L^1$, $L^2$ and $L^3$ is independently a bond or a $C_{1-6}$alkyl wherein 1 or 2 carbon atoms of the $C_{1-6}$alkyl are optionally replaced by a —O—, —C(O)—, —C(O)NR'—, —S—, —S(O)—, —S(O)$_2$—, —S(O)$_2$NR'— or —NR'—, wherein R' is H or $C_{1-5}$alkyl, and
 wherein the $C_{1-6}$alkyl is optionally substituted with 1 or 2 substituents selected from the group consisting of —OH, —SH, —NH$_2$, heterocyclyl, aryl and heteroaryl;
 V is —N$_3$;
 X is 1-oxypyrrolidine-2,5-dione or 1-oxycarbonyl-2,5-dione;
 Y is maleimidyl or —C(O)CH$_2$CH$_2$-maleimidyl; and each m, n and p is 1.

In another embodiment, there is provided a compound of the formula II

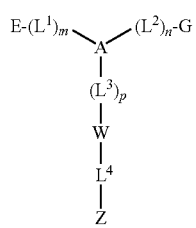

wherein:
 A is a low molecular weight scaffold selected from the group consisting of functionalized monocyclic and polycyclic hydrocarbons, functionalized monocyclic and polycyclic heterocycles, an amino acid residue, linear peptides, cyclic peptides, synthetic peptides, semi synthetic peptides, peptidomimetics and hyaluronic acid, and derivatives thereof;
 each $L^1$, $L^2$, $L^3$ and $L^4$ is independently a bond, a linker selected from the group consisting of an amino acid residue, —O—, —S—, —S(O)—, —S(O)$_2$—, —NR$^a$—, $C_{1-6}$alkyl, and —(CH$_2$CH$_2$O)$_{1-15}$, wherein R$^a$ is H or $C_{1-5}$alkyl, heterocyclyl, aryl, and heteroaryl, and
 wherein 1 or 2 carbon atoms of the $C_{1-6}$alkyl are optionally replaced by a —O—, —C(O)—, —C(O)NR'—, —S—, —S(O)—, —S(O)$_2$—, —S(O)$_2$NR' or —NR'—, wherein R' is H or $C_{1-5}$alkyl, and wherein the $C_{1-6}$alkyl is optionally substituted with 1 or 2 substituents selected from the group consisting of —OH, —SH, —NH$_2$, heterocyclyl, aryl and heteroaryl;
 E is a targeting agent;
 G is a chemotherapeutic agent or an antibody;
 W is a triazole;
 Z is a moiety comprising a non-radioactive element, a radionuclide selected from the group consisting of positron or gamma emitter or a chelator of a positron or gamma emitter, said chelator optionally chelated to a positron or gamma emitter; and each m, n and p is independently an integer of 1 to 10; or a pharmaceutically acceptable salt thereof, optionally in the form of a single stereoisomer or mixtures of stereoisomers thereof.

In another embodiment, there is provided a compound of the formula IIa

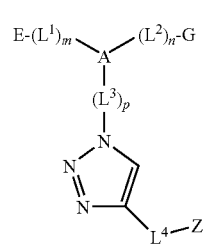

wherein:
 A is a low molecular weight scaffold selected from the group consisting of functionalized monocyclic and polycyclic hydrocarbons, functionalized monocyclic and polycyclic heterocycles, an amino acid residue, linear peptides, cyclic peptides, synthetic peptides, semi synthetic peptides, peptidomimetics and hyaluronic acid, and derivatives thereof;
 each $L^1$, $L^2$, $L^3$ and $L^4$ is independently a bond, a linker selected from the group consisting of an amino acid residue, —O—, —S—, —S(O)—, —S(O)$_2$—, —NR$^a$—, $C_{1-6}$alkyl, and —(CH$_2$CH$_2$O)$_{1-15}$, wherein R$^a$ is H or $C_{1-5}$alkyl, heterocyclyl, aryl, and heteroaryl, and
 wherein 1 or 2 carbon atoms of the $C_{1-6}$alkyl are optionally replaced by a —O—, —C(O)—, —C(O)NR'—, —S—, —S(O)—, —S(O)$_2$—, —S(O)$_2$NR' or —NR'—, wherein R' is H or $C_{1-5}$alkyl, and wherein the $C_{1-6}$alkyl is optionally substituted with 1 or 2 substituents selected from the group consisting of —OH, —SH, —NH$_2$, heterocyclyl, aryl and heteroaryl;
 E is a targeting agent;
 G is a chemotherapeutic agent or an antibody;

Z is a moiety comprising a non-radioactive element, a radionuclide selected from the group consisting of positron or gamma emitter or a chelator of a positron or gamma emitter, said chelator optionally chelated to a positron or gamma emitter; and each m, n and p is independently an integer of 1 to 10; or a pharmaceutically acceptable salt thereof, optionally in the form of a single stereoisomer or mixtures of stereoisomers thereof.

In another embodiment, there is provided a compound of the formula IIb

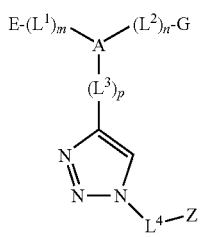

wherein:
A is a low molecular weight scaffold selected from the group consisting of functionalized monocyclic and polycyclic hydrocarbons, functionalized monocyclic and polycyclic heterocycles, an amino acid residue, linear peptides, cyclic peptides, synthetic peptides, semisynthetic peptides, peptidomimetics and hyaluronic acid, and derivatives thereof;

each $L^1$, $L^2$, $L^3$ and $L^4$ is independently a bond, a linker selected from the group consisting of an amino acid residue, —O—, —S—, —S(O)—, —S(O)$_2$—, —NR$^a$—, $C_{1-6}$alkyl, and —(CH$_2$CH$_2$O)$_{1-15}$, wherein $R^a$ is H or $C_{1-5}$alkyl, heterocyclyl, aryl, and heteroaryl, and wherein 1 or 2 carbon atoms of the $C_{1-6}$alkyl are optionally replaced by a —O—, —C(O)—, —C(O)NR'—, —S—, —S(O)—, —S(O)$_2$—, —S(O)$_2$NR' or —NR'—, wherein R' is H or $C_{1-5}$alkyl, and wherein the $C_{1-6}$alkyl is optionally substituted with 1 or 2 substituents selected from the group consisting of —OH, —SH, —NH$_2$, heterocyclyl, aryl and heteroaryl;

E is a targeting agent;
G is a chemotherapeutic agent or an antibody;
Z is a moiety comprising a non-radioactive element, a radionuclide selected from the group consisting of positron or gamma emitter or a chelator of a positron or gamma emitter, said chelator optionally chelated to a positron or gamma emitter; and each m, n and p is independently an integer of 1 to 10; or a pharmaceutically acceptable salt thereof, optionally in the form of a single stereoisomer or mixtures of stereoisomers thereof.

In one embodiment, A is selected from the group consisting of an amino acid residue, linear peptides, cyclic peptides, synthetic peptides, semisynthetic peptides, peptidomimetics and derivatives thereof.

In another embodiment, A is an amino acid residue or a dipeptide.

In yet another embodiment, A is a lysine residue.

In another embodiment, A is selected from the group consisting of an amino acid residue, linear peptides, cyclic peptides, synthetic peptides, semisynthetic peptides, peptidomimetics and derivatives thereof;

each $L^1$, $L^2$, $L^3$ and $L^4$ is independently a bond or a $C_{1-6}$alkyl wherein 1 or 2 carbon atoms of the $C_{1-6}$alkyl are optionally replaced by a —O—, —C(O)—, —C(O)NR'—, —S—, —S(O)—, —S(O)$_2$—, —S(O)$_2$NR'— or —NR'—, wherein R' is H or $C_{1-5}$alkyl, and wherein the $C_{1-6}$alkyl is optionally substituted with 1 or 2 substituents selected from the group consisting of —OH, —SH, —NH$_2$, heterocyclyl, aryl and heteroaryl; and each m, n and p is 1.

In a particular embodiment, A is selected from the group consisting of functionalized monocyclic and polycyclic hydrocarbons, functionalized monocyclic and polycyclic heterocycles, an amino acid residue, linear peptides, cyclic peptides, synthetic peptides, semisynthetic peptides, peptidomimetics and hyaluronic acid, and derivatives thereof;

each $L^1$, $L^2$ and $L^3$ is independently a bond or a $C_{1-6}$alkyl wherein 1 or 2 carbon atoms of the $C_{1-6}$alkyl is replaced by a —O—, —C(O)—, —C(O)NR'—, —S—, —S(O)—, —S(O)$_2$—, —S(O)$_2$NR'— or —NR'—, wherein R' is H or $C_{1-5}$alkyl, and wherein the $C_{1-6}$alkyl is optionally substituted with 1 or 2 substituents selected from the group consisting of —OH, —SH, —NH$_2$, heterocyclyl, aryl and heteroaryl;

$L^4$ is a $C_{1-6}$alkyl wherein 1 or 2 carbon atoms of the $C_{1-6}$alkyl are optionally replaced by a —O—, —C(O)—, —C(O)NR'—, —S—, —S(O)—, —S(O)$_2$—, —S(O)$_2$NR'— or —NR'—, wherein R' is H or $C_{1-5}$alkyl, and wherein the $C_{1-6}$alkyl is optionally substituted with 1 or 2 substituents selected from the group consisting of —OH, —SH, —NH$_2$, heterocyclyl, aryl and heteroaryl;

E is an RGD derivative or a CA-IX ligand;
G is a chemotherapeutic agent or an antibody;
W is a triazole; and
Z comprises a non-radioactive element, a radionuclide selected from the group consisting of positron or gamma emitter or a chelator of a positron or gamma emitter, said chelator optionally chelated to a positron or gamma emitter; and each of m, n and p is 1.

In one embodiment, the chemotherapeutic agent is selected from the group consisting of doxorubicin, cyclophosphamide, vincristine, streptozotocin, bevacizumab, prednisone and paclitaxel.

In another embodiment, the antibody is a catalytic antibody.

In yet another embodiment, the non-radioactive element is selected from the group consisting of F, I and Br, and the radionuclide is selected from the group consisting of $^{11}$C, $^{13}$N, $^{15}$O, $^{18}$F, $^{61}$Cu, $^{62}$Cu, $^{64}$Cu, $^{67}$Cu, $^{68}$Ga, $^{124}$I, $^{125}$I, $^{131}$I, $^{99}$Tc, $^{75}$Br, $^{153}$Gd and $^{32}$P.

In still another embodiment, the radionuclide is selected from the group consisting of $^{11}$C, $^{18}$F, $^{125}$I and $^{64}$Cu.

In another embodiment, there is provided a pharmaceutical composition comprising a therapeutically effective amount of a compound of formulas (I) or (II), and a pharmaceutically acceptable excipient, optionally in the form of a single stereoisomer or mixture of stereoisomers thereof.

In yet another embodiment, there is provided a method for treating cancer in a patient in need of such treatment, the method comprising: a) prequalifying a patient's therapeutic treatment by performing a molecular imaging procedure to the patient using a labeled biomarker specific for a cancer target at the tumor site; and b) administering a therapeutic effective amount of a compound comprising a targeting agent linked to a chemotherapeutic or a targeting agent linked to an antibody.

In a particular embodiment, the molecular imaging procedure is positron emission tomography (PET).

In another embodiment, the compound is a compound or composition of any one of the above compounds.

In still another embodiment, the therapeutically effective amount is effective to treat cancer.

Also included in the embodiments of the invention are salts of amino acids such as arginate and the like, gluconate, and galacturonate. Some of the compounds of the invention may form inner salts or zwitterions. Certain of the compounds of the present invention may also exist in unsolvated forms as well as solvated forms, including hydrated forms, and are intended to be within the scope of the present invention. Certain of the above compounds may also exist in one or more solid or crystalline phases or polymorphs, the variable biological activities of such polymorphs or mixtures of such polymorphs are also included within the scope of this invention. Also provided are pharmaceutical compositions comprising pharmaceutically acceptable excipients and a therapeutically effective amount of at least one compound of the invention.

Pharmaceutical compositions of the compounds of the invention, or derivatives thereof, may be formulated as solutions or lyophilized powders for parenteral administration. Powders may be reconstituted by addition of a suitable diluent or other pharmaceutically acceptable carrier prior to use. The liquid formulation may generally exist as a buffered, isotonic, aqueous solution. Non-limiting examples of suitable diluents are normal isotonic saline solution, 5% dextrose in water or buffered sodium, or ammonium acetate solution. Such formulations are especially suitable for parenteral administration, but may also be used for oral administration. Excipients, such as, by way of non-limiting example, polyvinylpyrrolidinone, gelatin, hydroxycellulose, acacia, polyethylene glycol, mannitol, sodium chloride or sodium citrate, may also be added. Alternatively, these compounds may be encapsulated, tableted, or prepared in an emulsion or syrup for oral administration. Pharmaceutically acceptable solid or liquid carriers may be added to enhance or stabilize the composition, or to facilitate preparation of the composition. Non-limiting examples of liquid carriers may include syrup, peanut oil, olive oil, glycerin, saline, alcohols, and/or water. Non-limiting examples of solid carriers may include starch, lactose, calcium sulfate, dihydrate, terra alba, magnesium stearate or stearic acid, talc, pectin, acacia, agar, and/or gelatin. The carrier may also include a sustained release material such as, for example glyceryl monostearate or glyceryl distearate, alone or with a wax. The amount of solid carrier varies but, preferably, will be between about 20 mg to about 1 g per dosage unit. The pharmaceutical preparations may be made following the conventional techniques of pharmacy involving, by way of non-limiting example, milling, mixing, granulation, and compressing, when necessary, for tablet forms; or milling, mixing, and filling for hard gelatin capsule forms. When a liquid carrier is used, the preparation may be in the form of, by way of non-limiting example, a syrup, elixir, emulsion, or an aqueous or non-aqueous suspension. Such a liquid formulation may be administered directly p.o. or filled into a soft gelatin capsule. Suitable formulations for each of these methods of administration may be found in, by way of non-limiting example, *Remington: The Science and Practice of Pharmacy*, A. Gennaro, ed., 20th edition, Lippincott, Williams & Wilkins, Philadelphia, Pa.

In one embodiment, the compounds of the invention, or a pharmaceutically acceptable salt thereof, may exist in the form of a single stereoisomer or mixture of stereoisomers thereof.

In another embodiment, the compounds of the invention, or a pharmaceutically acceptable salt thereof, may exist in the form of a mixture of stereoisomers.

Unless specifically noted otherwise herein, the definitions of the terms used are standard definitions used in the art of organic synthesis and pharmaceutical sciences. Exemplary embodiments, aspects and variations are illustrated in the figures and drawings, and it is intended that the embodiments, aspects and variations, and the figures and drawings disclosed herein are to be considered illustrative and not limiting.

An "alkyl" group is a straight, branched, saturated or unsaturated, aliphatic group having a chain of carbon atoms, optionally with oxygen, nitrogen or sulfur atoms inserted between the carbon atoms in the chain or as indicated. Alkyl groups may be optionally substituted. An alkyl group may include a $(C_1$-$C_{20})$alkyl. A $(C_1$-$C_6)$alkyl, by way of non-limiting example, includes alkyl groups that have a chain of between 1 and 6 carbon atoms, and include, by way of non-limiting example, the groups methyl, ethyl, propyl, isopropyl, vinyl, allyl, 1-propenyl, isopropenyl, ethynyl, 1-propynyl, 2-propynyl, 1,3-butadienyl, penta-1,3-dienyl, and the like. An alkyl group, such as a "$C_1$-$C_6$ alkyl," that forms a part of a group or linker is a divalent alkyl group, and also may be referred to as an "alkylene" group. Similarly, an alkenyl group, alkynyl group, aryl group, etc in a structure that is shown as a divalent group may be referred to as an alkenylenyl, alkynylenyl, arylenyl group respectively.

An alkyl as noted with another group such as an aryl group, represented as "arylalkyl" for example, is intended to be a straight, branched, saturated or unsaturated aliphatic divalent group with the number of atoms indicated in the alkyl group (as in $(C_1$-$C_6)$alkyl, by way of non-limiting example) and/or aryl group or when no atoms are indicated means a bond between the aryl and the alkyl group. Nonexclusive examples of such groups include benzyl, phenylethyl and the like.

An "alkylene" group or "alkylenyl group" is a straight, branched, saturated or unsaturated aliphatic divalent group with the number of atoms indicated in the alkyl group; for example, but not limited to, a —$(C_1$-$C_3)$alkylene- or —$(C_1$-$C_3)$alkylenyl-.

The term "alkenyl" refers to unsaturated groups which contain at least one carbon-carbon double bond and includes straight-chain, branched-chain and cyclic groups. Alkene groups may be optionally substituted. Exemplary groups include, but are not limited to, 1-butenyl, 2-butenyl, 3-butenyl, isobutenyl, 1-propenyl, 2-propenyl and ethenyl.

The term "alkoxy" or "alkyloxy" includes linear or branched alkyl groups that are attached to divalent oxygen. The alkyl group is as defined above. Examples of such substituents include, but are not limited to, methoxy, ethoxy, t-butoxy, and the like. The term "alkoxyalkyl" refers to an alkyl group that is substituted with one or more alkoxy groups. Alkoxy groups may be optionally substituted. The term "aryloxy" refers to an aryl group that is attached to an oxygen, such as phenyl-O—, etc.

The term "alkynyl" refers to unsaturated groups which contain at least one carbon-carbon triple bond and includes straight-chain, branched-chain and cyclic groups. Alkyne groups may be optionally substituted. Exemplary groups include, but are not limited to, 1-butynyl, 2-butynyl, 3-butynyl, 1-propynyl, 2-propynyl and ethynyl.

The term "carbocycle" (or carbocyclyl) as used herein refers to a $C_3$ to $C_8$ monocyclic, saturated, partially saturated or aromatic ring. Carbocycles may be optionally substituted. Non-exclusive examples of carbocycle include cyclopropane, cyclobutane, cyclopentane, cyclohexane, cycloheptane, cyclopentene, cyclohexene, cycloheptene, cyclooctene, benzyl, naphthene, anthracene, phenanthracene, biphenyl and pyrene.

A "heterocyclyl" or "heterocycle" is a carbocycle group wherein one or more of the atoms forming the ring is a heteroatom that is a N, O, or S. The heterocycle may be saturated, partially saturated or aromatic. Heterocycles may be optionally substituted. Non-exclusive examples of heterocyclyl (or heterocycle) include piperidyl, 4-morpholyl, 4-piperazinyl, pyrrolidinyl, 1,4-diazaperhydroepinyl, acetonidyl-4-one, 1,3-dioxanyl, thiophenyl, furanyl, pyrrolyl, pyrazolyl, pyridinyl, pyrimidinyl, pyridazinyl, pyranyl and the like.

A "cyclyl" such as a monocyclyl or polycyclyl group includes monocyclic, or linearly fused, angularly fused or bridged polycycloalkyl, or combinations thereof. Such cyclyl group is intended to include the heterocyclyl analogs. A cyclyl group may be saturated, partially saturated or aromatic.

"Halogen" or "halo" means fluorine, chlorine, bromine or iodine.

The term "optionally substituted" or "substituted" refers to the specific group wherein one to four hydrogen atoms in the group may be replaced by one to four substituents, independently selected from, but not limited to, alkyl, aryl, alkylenearyl, hydroxy, alkoxy, aryloxy, perhaloalkoxy, heterocycle, azido, amino, guanidino, amidino, halo, alkylthio, oxo, acylalkyl, carboxy esters, carboxyl, carboxamido, nitro, acyloxy, aminoalkyl, alkylaminoaryl, alkylaminoalkyl, alkoxyaryl, arylamino, phosphono, sulfonyl, carboxamidoaryl, hydroxyalkyl, haloalkyl, cyano, alkoxyalkyl, and perhaloalkyl. In addition, the term "optionally substituted" or "substituted," including in reference to the moiety Z, includes groups substituted by one to four substituents, as identified above, or that comprises a metal chelating agent or moiety, that further comprise a positron or gamma emitter. Such positron emitters include, but are not limited to $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$, $^{131}I$, $^{99}Tc$, $^{75}Br$, $^{153}Gd$ and $^{32}P$.

As used herein, the term "side chain" of a natural or unnatural amino acid refers to "Q" group in the amino acid formula, as exemplified by $NH_2CH(Q)CO_2H$.

As used herein, the term "polar amino acid moiety" refers to the side chain, Q, of a polar natural or unnatural amino acid. Polar natural amino acids include, but are not limited to, arginine, asparagine, aspartic acid, cysteine, glutamic acid, glutamine, histidine and lysine.

As used herein, "natural amino acid" refers to the naturally occurring amino acids: glycine, alanine, valine, leucine, isoleucine, serine, methionine, threonine, phenylalanine, tyrosine, tryptophan, cysteine, proline, histidine, aspartic acid, asparagine, glutamic acid, glutamine, arginine and lysine.

The term "unnatural amino acid" refers to any derivative of a natural amino acid including, for example, D and L forms, and α- and β-amino acid derivatives. It is noted that certain amino acids, e.g., hydroxyproline, that are classified as a non-natural amino acid herein, may be found in nature within a certain organism or a particular protein. The following non-exclusive examples of non-natural amino acids and amino acid derivatives may be used according to the application (common abbreviations in parentheses): β-alanine (β-ALA), γ-aminobutyric acid (GABA), ornithine, 2-aminobutyric acid (2-Abu), β-dehydro-2-aminobutyric acid (8-AU), 1-aminocyclopropane-1-carboxylic acid (ACPC), aminoisobutyric acid (Aib), γ-carboxyglutamic acid, 2-amino-thiazoline-4-carboxylic acid, 5-aminovaleric acid (5-Ava), 6-aminohexanoic acid (6-Ahx), 8-aminooctanoic acid (8-Aoc), 11-aminoundecanoic acid (11-Aun), 12-aminododecanoic acid (12-Ado), 2-aminobenzoic acid (2-Abz), 3-aminobenzoic acid (3-Abz), 4-aminobenzoic acid (4-Abz), 4-amino-3-hydroxy-6-methylheptanoic acid (Statine, Sta), aminooxyacetic acid (Aoa), 2-aminotetraline-2-carboxylic acid (ATC), 4-amino-5-cyclohexyl-3-hydroxypentanoic acid (ACHPA), para-aminophenylalanine (4-$NH_2$-Phe), biphenylalanine (Bip), para-bromophenylalanine (4-Br-Phe), ortho-chlorophenylalanine (2-Cl-Phe), meta-chlorophenylalanine (3-Cl-Phe), para-chlorophenylalanine (4-Cl-Phe), meta-chlorotyrosine (3-Cl-Tyr), para-benzoylphenylalanine (Bpa), tert-butylglycine (TLG), cyclohexylalanine (Cha), cyclohexylglycine (Chg), 2,3-diaminopropionic acid (Dpr), 2,4-diaminobutyric acid (Dbu), 3,4-dichlorophenylalanine (3,4-$Cl_2$-Phe), 3,4-difluorophenylalanine (3,4-$F_2$-Phe), 3,5-diiodotyrosine (3,5-$I_2$-Tyr), ortho-fluorophenylalanine (2-F-Phe), meta-fluorophenylalanine (3-F-Phe), para-fluorophenylalanine (4-F-Phe), meta-fluorotyrosine (3-F-Tyr), homoserine (Hse), homophenylalanine (Hfe), homotyrosine (Htyr), 5-hydroxytryptophan (5-OH-Trp), hydroxyproline (Hyp), para-iodophenylalanine (4-I-Phe), 3-iodotyrosine (3-I-Tyr), indoline-2-carboxylic acid (Idc), isonipecotic acid (Inp), meta-methyltyrosine (3-Me-Tyr), 1-naphthylalanine (1-Nal), 2-naphthylalanine (2-Nal), para-nitrophenylalanine (4-$NO_2$-Phe), 3-nitrotyrosine (3-$NO_2$-Tyr), norleucine (Nle), norvaline (Nva), ornithine (Orn), ortho-phosphotyrosine ($H_2PO_3$-Tyr), octahydroindole-2-carboxylic acid (Oic), penicillamine (Pen), pentafluorophenylalanine ($F_5$-Phe), phenylglycine (Phg), pipecolic acid (Pip), propargylglycine (Pra), pyroglutamic acid (PGLU), sarcosine (Sar), tetrahydroisoquinoline-3-carboxylic acid (Tic), thienylalanine, and thiazolidine-4-carboxylic acid (thioproline, Th). Additionally, N-alkylated amino acids may be used, as well as amino acids having amine-containing side chains (such as Lys and Orn) in which the amine has been acylated or alkylated.

The term "protecting group" or "PG" as used herein is intended to be defined as commonly practiced by the skilled artisan. Non-limiting examples of protecting groups are summarized in Greene et al., *Protective Groups in Organic Synthesis*, Second Edition, John Wiley and Sons, New York, 1991. Judicious choice of protecting groups may be dependant on the particular synthetic methods and routes employed, and may be governed by the skilled artisan. When multiple protecting groups are present in a molecule, they may or may not be identical, depending on their specific purpose and the scenario of the synthetic method.

"Linker" as used herein, or as specifically defined herein, including the groups "$L^1$", "$L^2$", "$L^3$", "$L^4$", and "A", refers to a chain comprising 1 to 200 atoms and may comprise atoms or groups, such as, but not limited to, C, —NR—, O, S, —S(O)—, —S(O)$_2$—, CO, —C(NR)—, a polyethylene glycol (PEG) moiety, and the like, and wherein R is H or is selected from the group consisting of ($C_{1-10}$)alkyl, ($C_{3-8}$) cycloalkyl, aryl($C_{1-5}$)alkyl, heteroaryl($C_{1-5}$)alkyl, amino, aryl, heteroaryl, hydroxy, ($C_{1-10}$)alkoxy, aryloxy, heteroaryloxy, each substituted or unsubstituted. The linker chain may also comprise part of a saturated, unsaturated or aromatic ring, including, but not limited to, monocyclic (e.g. a 1,5-cyclohexylenyl group, sugar mimetic, and sugar moiety), polycyclic and heteroaromatic rings (e.g. a 2,4-pyridinyl group etc . . . ). The representation of "($C_{1-3}$)alkyl", for example, is used interchangeably with "$C_1$-$C_3$alkyl" to mean the same.

As used herein, where a divalent group, such as a linker, is represented by a generic structure -A-B-, as shown below, it is intended to also represent a group that may be attached in both possible permutations, as noted in the two structures as follows:

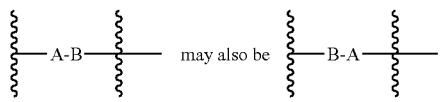

A "mimetic" of a peptidic structure includes compounds in which chemical structures of the peptidic structure necessary for functional activity of the peptidic structure have been replaced with other chemical structures which mimic the conformation of the peptidic structure. The term "mimetic", and in particular, peptidomimetic, includes isosteres. The term "isostere" includes chemical structures that can be substituted for a second chemical structure because the steric conformation of the first structure that may fit a binding site specific for the second structure. The term specifically includes peptide backbone modifications (i.e., amide bond mimetics) well-known to those skilled in the art. Such modifications include, by way of non-limiting example, modifications of the amide nitrogen, the α-carbon, amide carbonyl, complete replacement of the amide bond, extensions or deletions. Several peptide backbone modifications are known, including, but not limited to, ψ[CH$_2$S], ψ[CH$_2$NH], ψ[CSNH], ψ[NHCO], ψ[COCH$_2$], and ψ[(E) or (Z) CH=CH]. As used herein, ψ indicates the absence of an amide bond. The structure that replaces the amide group is specified within the brackets. Other possible modifications include, but are not limited to, an N-alkyl (or aryl) substitution (ψ[CONR]). Non-limiting examples of other derivatives of the compounds include C-terminal hydroxymethyl derivatives, O-modified derivatives (e.g., C-terminal hydroxymethyl benzyl ether), N-terminally modified derivatives including substituted amides such as alkylamides and hydrazides and compounds in which a C-terminal phenylalanine structure is replaced with a phenethylamide analog (e.g., Val-Phe-phenethylamide as an analog of the tripeptide Val-Phe-Phe).

"Peptide mimetics" may be in their free acid form or may be amidated at the C-terminal carboxylate group. The homologs of the peptides as provided herein typically have structural similarity with such peptides. A "homolog" of a polypeptide includes one or more conservative amino acid substitutions, which may be selected from the same or different members of the class to which the amino acid belongs. By way of non-limiting example, an amino acid belonging to a grouping of amino acids having a particular size or characteristic (such as charge, hydrophobicity and hydrophilicity) may generally be substituted for another amino acid without substantially altering the structure of a polypeptide.

Conservative amino acid substitutions are defined to result from exchange of amino acids residues from within one of the following classes of residues: Class I: Ala, Gly, Ser, Thr and Pro (representing small aliphatic side chains and hydroxyl group side chains); Class II: Cys, Ser, Thr and Tyr (representing side chains including an —OH or —SH group); Class III: Glu, Asp, Asn and Gln (carboxyl group containing side chains): Class IV: His, Arg and Lys (representing basic side chains); and Class V: Ile, Val, Leu, Phe, Met, Phe, Trp, Tyr and His (representing hydrophobic side chains). The classes also include related amino acids such as, but not limited to, 3Hyp and 4Hyp in Class I; homocysteine in Class II; 2-aminoadipic acid, 2-aminopimelic acid, γ-carboxyglutamic acid, β-carboxyaspartic acid, and the corresponding amino acid amides in Class III; ornithine, homoarginine, N-methyl lysine, dimethyl lysine, trimethyl lysine, 2,3-diaminopropionic acid, 2,4-diaminobutyric acid, homoarginine, sarcosine and hydroxylysine in Class IV; substituted phenylalanines, norleucine, norvaline, 2-aminooctanoic acid, 2-aminoheptanoic acid, statine and β-valine in Class V; and naphthylalanines, substituted phenylalanines, tetrahydroisoquinoline-3-carboxylic acid and halogenated tyrosines in Class V.

Head-to-tail (backbone) peptide cyclization has been used to rigidify the structure of small peptides (see Camarero and Muir, J. Am. Chem. Soc., 121:5597-5598 (1999)). Hruby, V. J., et al., "Conformational restrictions of biologically active peptides via amino acid side chain groups," Life Sci. 31(3): 189-199 (July 1982). Koivunen, E., et al., "Phage libraries displaying cyclic peptides with different ring sizes: ligand specificities of the RGD-directed integrins," Biotechnology 13(3):265-270 (March 1995). Zhang, L., et al., "Synthesis and Application of Unprotected Cyclic Peptides as Building Blocks for Peptide Dendrimers," J. Am. Chem. Soc. 119(10): 2363-2370 (March 1997). Scott, C., et al. Structural requirements for the biosynthesis of backbone cyclic peptide libraries. Chemistry and Biology. 2001, vol. 8, pp. 801-815.

"Polypeptide homologs" include modified polypeptides. Modifications of polypeptides include, but are not limited to, chemical and/or enzymatic derivatizations at one or more constituent amino acid, including side chain modifications, backbone modifications, and N- and C-terminal modifications including acetylation, hydroxylation, methylation, amidation, and the attachment of carbohydrate or lipid moieties, cofactors and the like.

"Catalytic antibodies" refers to large proteins that are naturally produced by the immune system and have the capability of initiating diverse chemical reactions similarly to enzymes. Catalytic antibodies are elicited against small molecules that are bound to carrier proteins and contain a specific binding site. In their native form, catalytic antibodies are constructed of two pairs of polypeptide chains that differ in length and are connected to each other by disulfide bridges. Various antibody molecules are known in the art, and share a common structure, but they differ in the N-terminal regions of antibody light and heavy chains which are responsible for antigen recognition. These regions vary greatly in the sequence and number of their constituent amino acids and therefore provide an enormous diversity of antigen-binding domains.

Chemotherapeutic agents may be agents for treatment of a variety of afflictions and diseases, including, but not limited to, central nervous system diseases, neurodegenerative diseases such as Alzheimer's or Parkinson's disease, cancers, autoimmune diseases such as HIV, cardiovascular diseases, inflammatory diseases, infectious diseases and the like. Examplary agents include, but are not limited to, anti-neoplastic agents, anti-angiogenic agents, anti-tumor agents, antimicrobial agents, antiviral agents, and antifungal agents.

Targeting agents may be compounds comprised of moieties that recognize, bind or adhere to a target moiety of a target molecule located, for example, in an organism, tissue, cell or extracellular fluid, or any combination thereof. Targeting agents include, but are not limited to, peptide targeting agents such as, for example, integrin targeting agents, proteins, antibodies, drugs, peptidomimetics, glycoproteins, glycolipids, glycans, lipids, nucleic acids, carbohydrates, phospholipids and the like. Targeting agents include, but are not limited to, organic molecules comprised of a mass of 5,000 daltons or less.

"Pharmaceutically acceptable salts" means salt compositions that are generally considered to have the desired pharmacological activity, are considered to be safe, non-toxic and acceptable for veterinary and human pharmaceutical applications. Non-limiting examples of such salts include acid addition salts formed with inorganic acids such as hydrochloric acid, hydrobromic acid, sulfuric acid, phosphoric acid, and the like; or with organic acids such as acetic acid, propionic acid, hexanoic acid, malonic acid, succinic acid, malic acid, citric acid, gluconic acid, salicylic acid and the like.

"Therapeutically effective amount" means a drug amount that elicits any of the biological effects listed in the specification.

"Substituted or unsubstituted" or "optionally substituted" means that a group such as, for example, but not limited to alkyl, aryl, heterocyclyl, $(C_1-C_8)$cycloalkyl, heterocyclyl($C_1$-$C_8$)alkyl, aryl($C_1$-$C_8$)alkyl, heteroaryl, heteroaryl($C_1$-$C_8$) alkyl, and the like, unless specifically noted otherwise, may be unsubstituted or, may substituted by 1, 2 or 3 substituents selected from the group such as, but not limited to, halo, nitro, trifluoromethyl, trifluoromethoxy, methoxy, ethoxy, carboxy, $—NH_2$, $—OH$, $—SH$, $—NHCH_3$, $—N(CH_3)_2$, $—SMe$, cyano and the like.

The following procedures may, by way of non-limiting example, be employed for the preparation of the compounds of the present invention. The starting materials and reagents used in preparing these compounds are either available from commercial suppliers such as the Aldrich Chemical Company (Milwaukee, Wis.), Bachem (Torrance, Calif.), Sigma (St. Louis, Mo.), or are prepared by methods well known to a person of ordinary skill in the art, following procedures described in such references including, but not limited to *Fieser and Fieser's Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; *Organic Reactions*, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

In some cases, protective groups may be introduced and finally removed. Suitable protective groups for amino, hydroxy, and carboxy groups are described, for example, in Greene et al., *Protective Groups in Organic Synthesis*, Second Edition, John Wiley and Sons, New York, 1991. Standard organic chemical reactions may be achieved using a number of different reagents including, but not limited to those described in Larock: *Comprehensive Organic Transformations*, VCH Publishers, New York, 1989.

In one embodiment, the Paint and Destroy conjugates may be prepared using a polyfunctional linker.

In one embodiment, the polyfunctional linker is generically represented as the variable "A".

In another embodiment, the polyfunctional linker may be a tri-functional linker (FIG. 3), the linker comprised of three sites for conjugation to link a targeting agent, a macromolecule and a radiolabeling site.

In one another embodiment, the three sites for conjugation may comprise an amine reactive moiety, a sulfur reactive moiety and an azide for both direct and indirect radiolabeling.

In one particular embodiment, as represented by a tri-functional linker, the linker may be readily assembled in four steps. Starting from a protected amino acid such as lysine (wherein PG is a protecting group, see, e.g. Greene et al., *Protective Groups in Organic Synthesis*, Second Edition, John Wiley and Sons, New York, 1991), the side chain amine may be acylated, for example via the N-Hydroxysuccinamide (NHS) ester of glycine azide (2) (Scheme 1). The protecting group may then be removed, followed by acylation of the amine group using, for example, a linker to afford the new maleimide derivative such as 6. Finally, the free acid may be activated as the NHS ester 8.

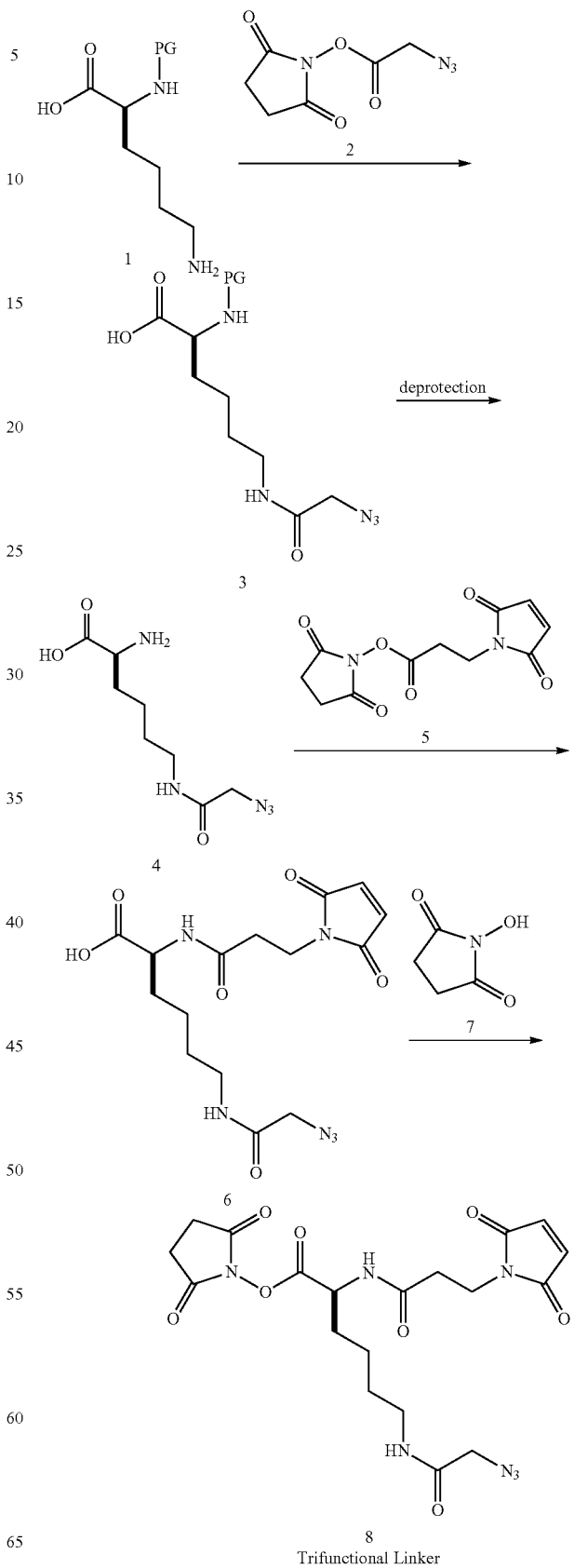

Scheme 1. General Synthesis of Lysine-derived Trifunctional Linkers.

8
Trifunctional Linker

In another particular embodiment, as represented by an alkyne-containing tri-functional linker, the linker may be readily assembled as shown, for example, in scheme 2. Starting from a protected amino acid derivative such as 9 (wherein PG is again a protecting group), the protecting group may be removed, followed by acylation of the amino group using, for example, a linker to afford a maleimide derivative such as 11. The free acid may then be activated as the NHS ester to provide an alkyne-derived trifunctional linker such as 12.

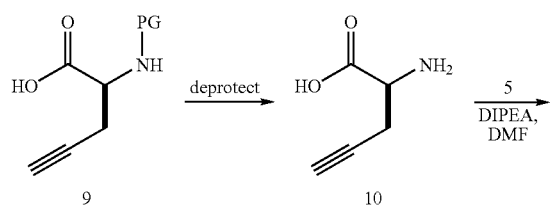

Scheme 2. General Synthesis of Alkyne-derived Trifunctional Linkers.

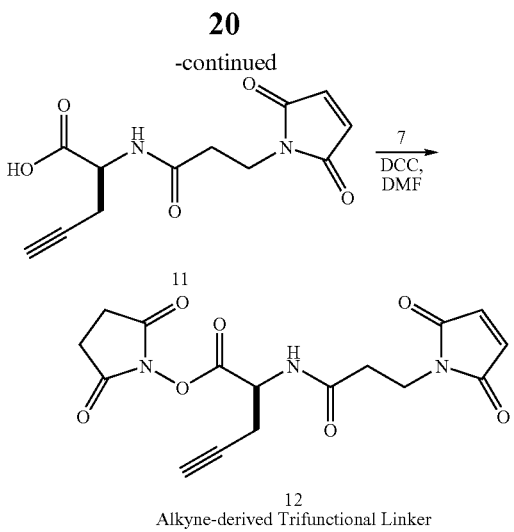

12
Alkyne-derived Trifunctional Linker

In another embodiment, as exemplified with schemes 3-5, the targeting agent may be first conjugated to a tri-functional linker, followed by conjugation of a macromolecule, and then followed by radiolabeling with a radionuclide such as 18F.

Scheme 3. General Synthesis of Polyfunctional Therapeutic Agents.

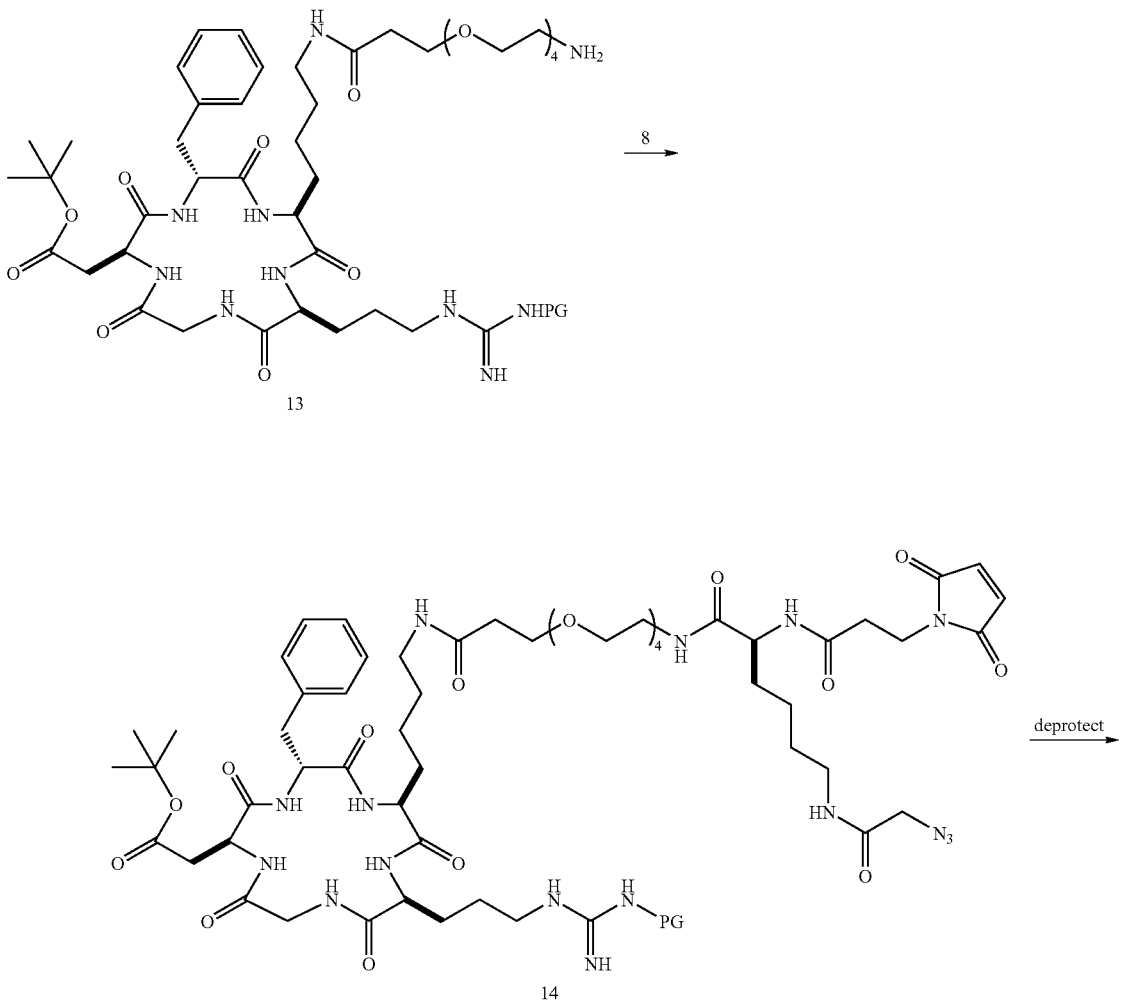

-continued
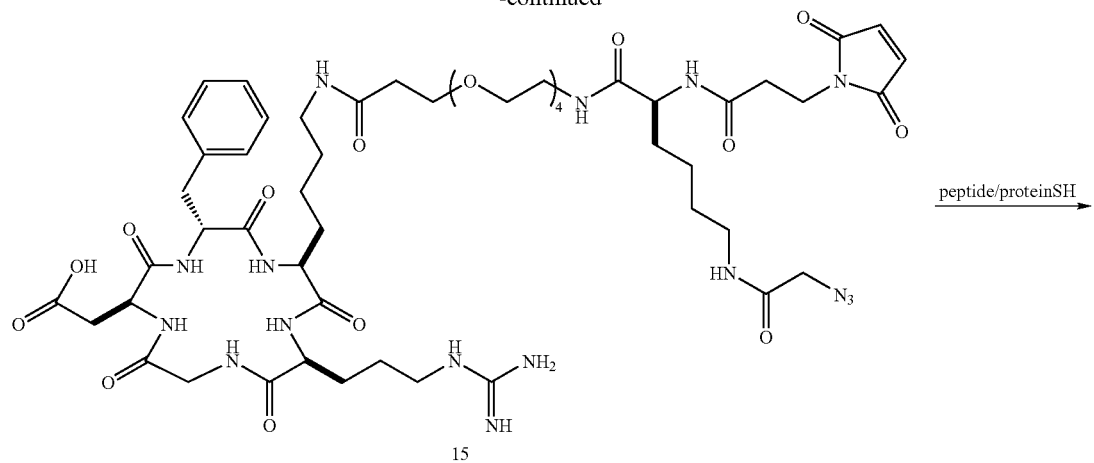
15
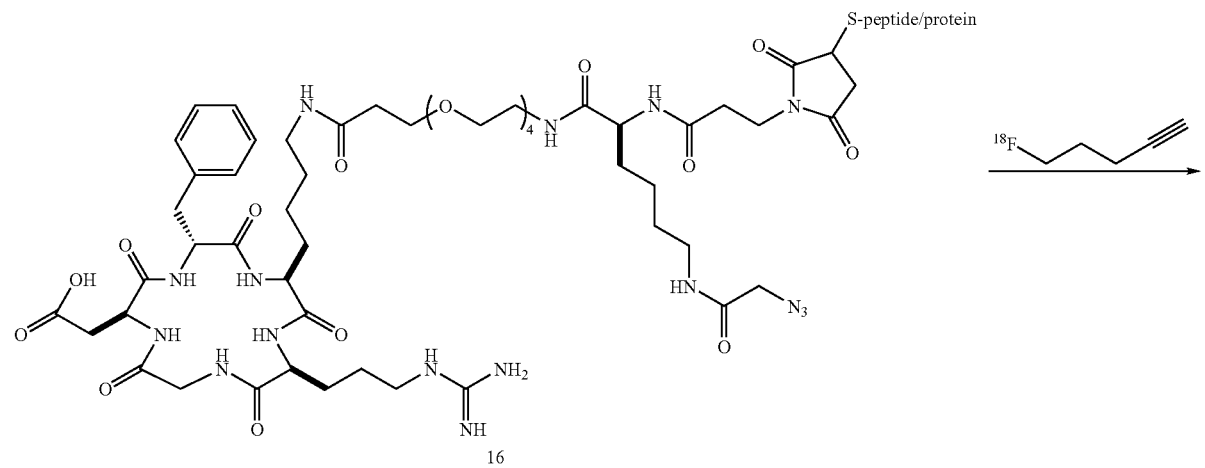
16
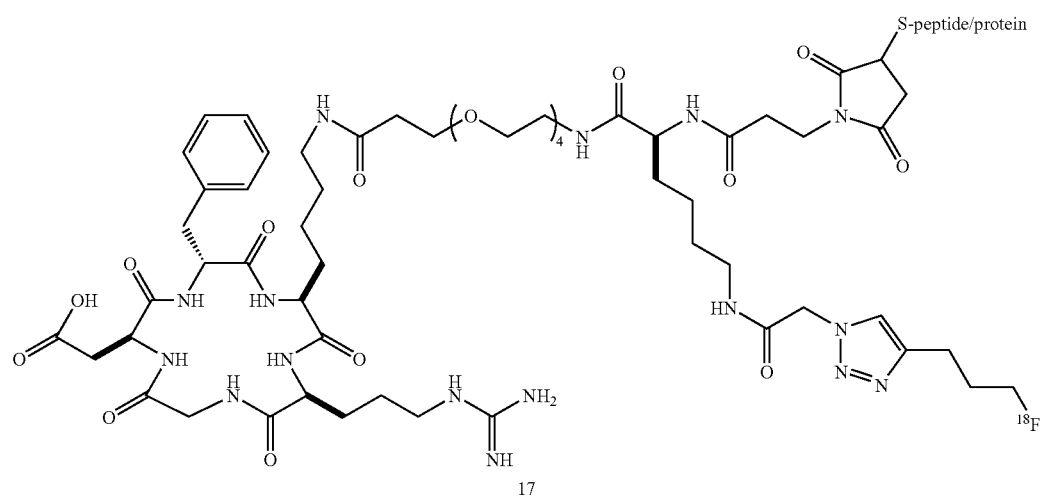
17

Scheme 4. General Synthesis of Polyfunctional Therapeutic Agents.
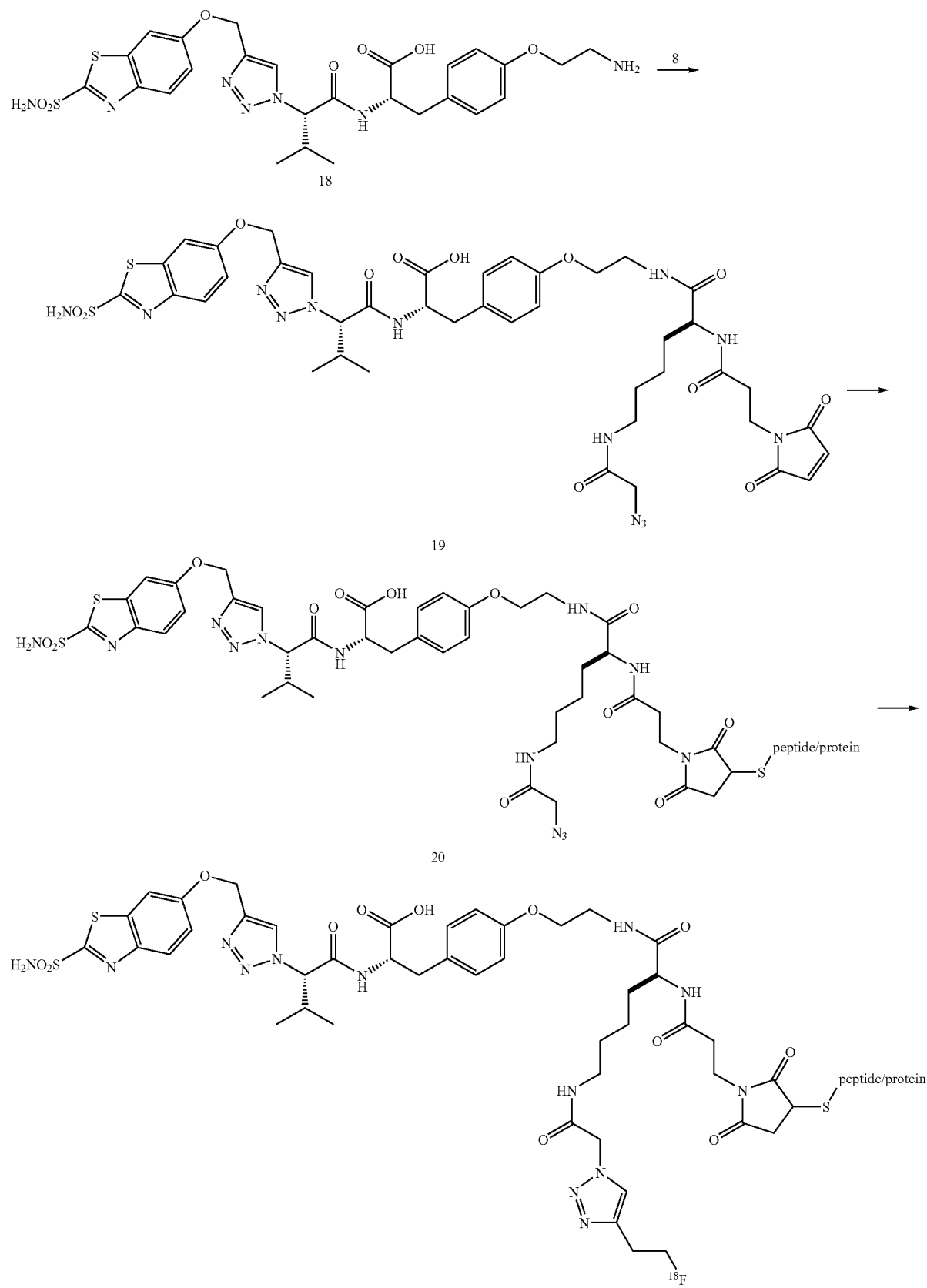

Scheme 5. General Synthesis of Polyfunctional Therapeutic Agents and Standards.

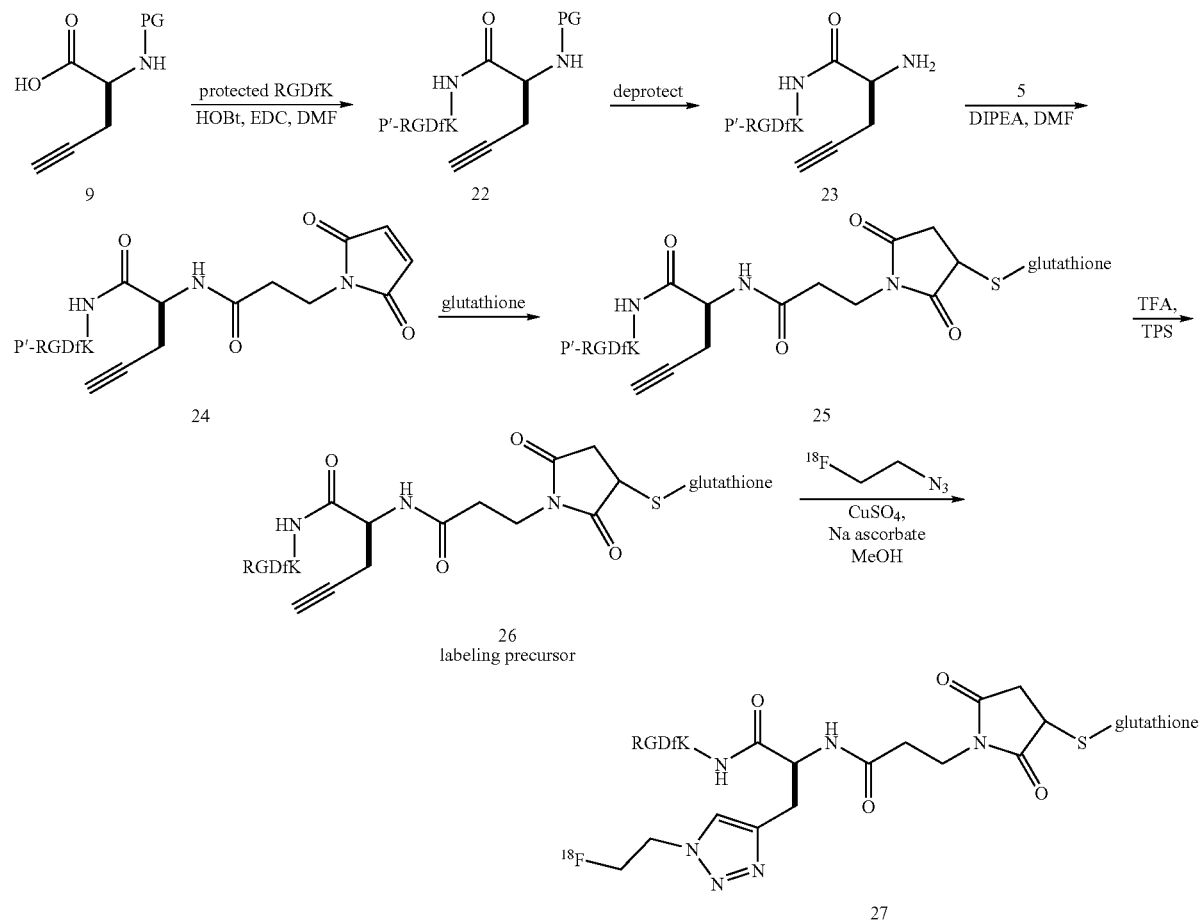

In yet another embodiment, the clearance properties of the macromolecule may be compatible with 18F-imaging.

In still another embodiment, non-radiolabeled standards may be synthesized using non-radiolabeled precursors and reagents. By way of non-limiting example, 19F may be used in lieu of 18F to provide a non-radiolabeled standard.

In yet another embodiment, the compound may include a substrate that chelates a radionuclide (Scheme 6). In this example, the targeting agent may be first conjugated to the linker, macromolecule is then conjugated to the compound comprising the targeting agent, and the chelating agent, such as 1,4,7,10-tetraazacyclododecane'-N,N',N'',N'''-tetraacetic acid (DOTA) and derivatives thereof, may be attached to the linker via a azide. In the chelation step, a radioactive metal (such as 64Cu) may be added to chelate to the DOTA group. Other chelators may be employed, including, but not limited to diethylenetriaminopentaacetic acid (DTPA) and derivatives thereof. See for example, U.S. Pat. Nos. 5,358,704; 5,262,532; 5,219,553; 5,188,816; 5,155,215; 5,087,440; 4,885,363; and Meyer, et al., Invest. Radiol. 25:S53 (1990).

Scheme 6. General Synthesis of Radionuclide Chelating Polyfunctional Therapeutic Agents.

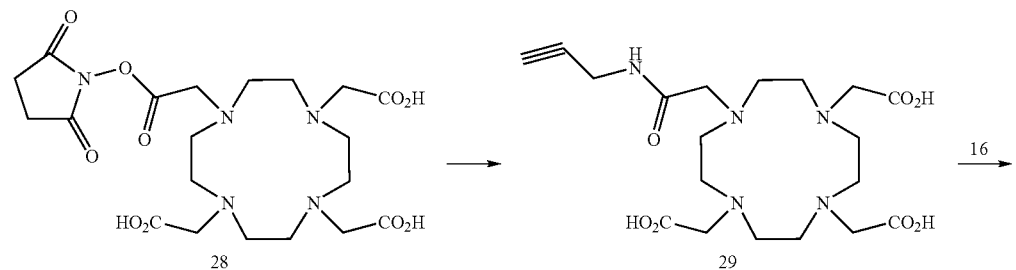

-continued

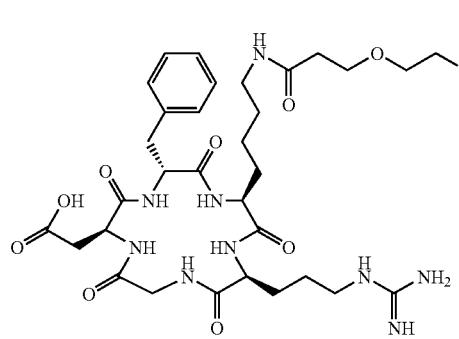
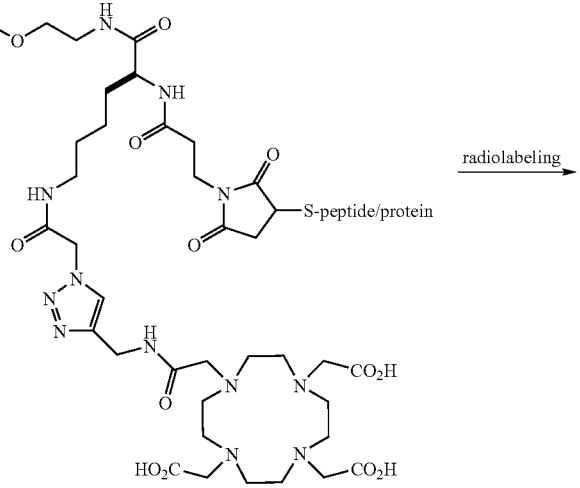

30

$\xrightarrow{\text{radiolabeling}}$

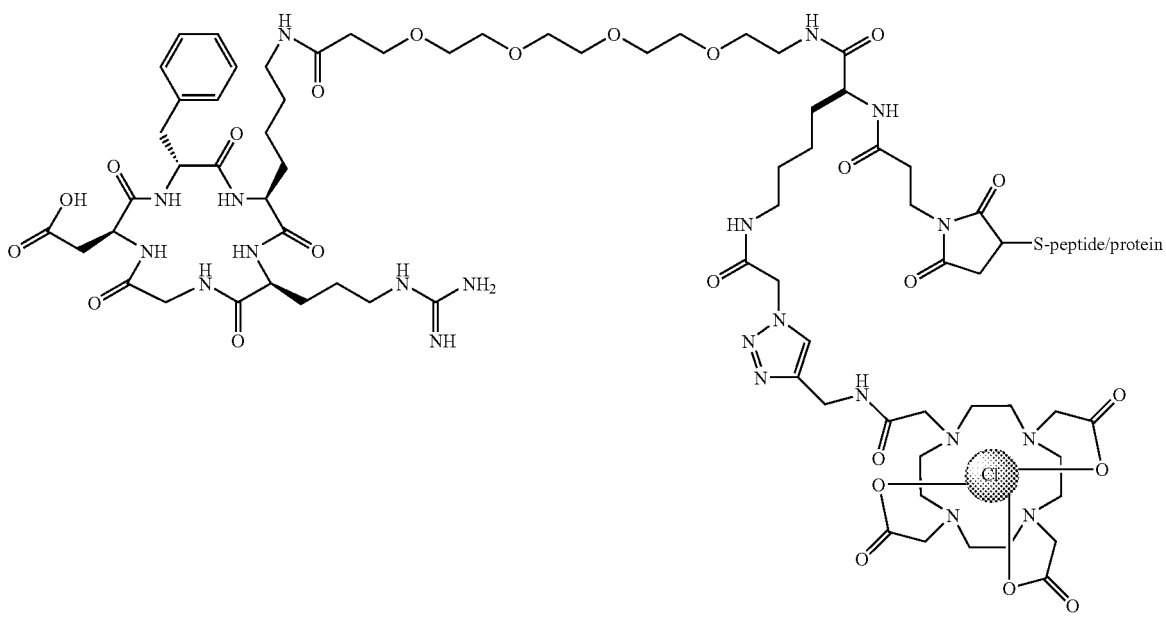

31

In still another embodiment, the targeting agent may be first conjugated to the linker, followed by attachment of an antibody tethering moiety (Guo, F.; Das, S.; Mueller, B. M.; Barbas III, C. F.; Lerner, R. A.; Sinha, S. *Proc. Natl. Acad. Sci.* 2006, 103, 11009-11014), and may be further followed by the attachment of DOTA to the linker via the azide (Scheme 7). The antibody may then be conjugated via attachment to the tethering moiety. In the final step, a radioactive metal (such as Cu-64) may be added to chelate to the DOTA group.

Scheme 7. General Synthesis of Polyfunctional Therapeutic Agents Comprising Antibodies.
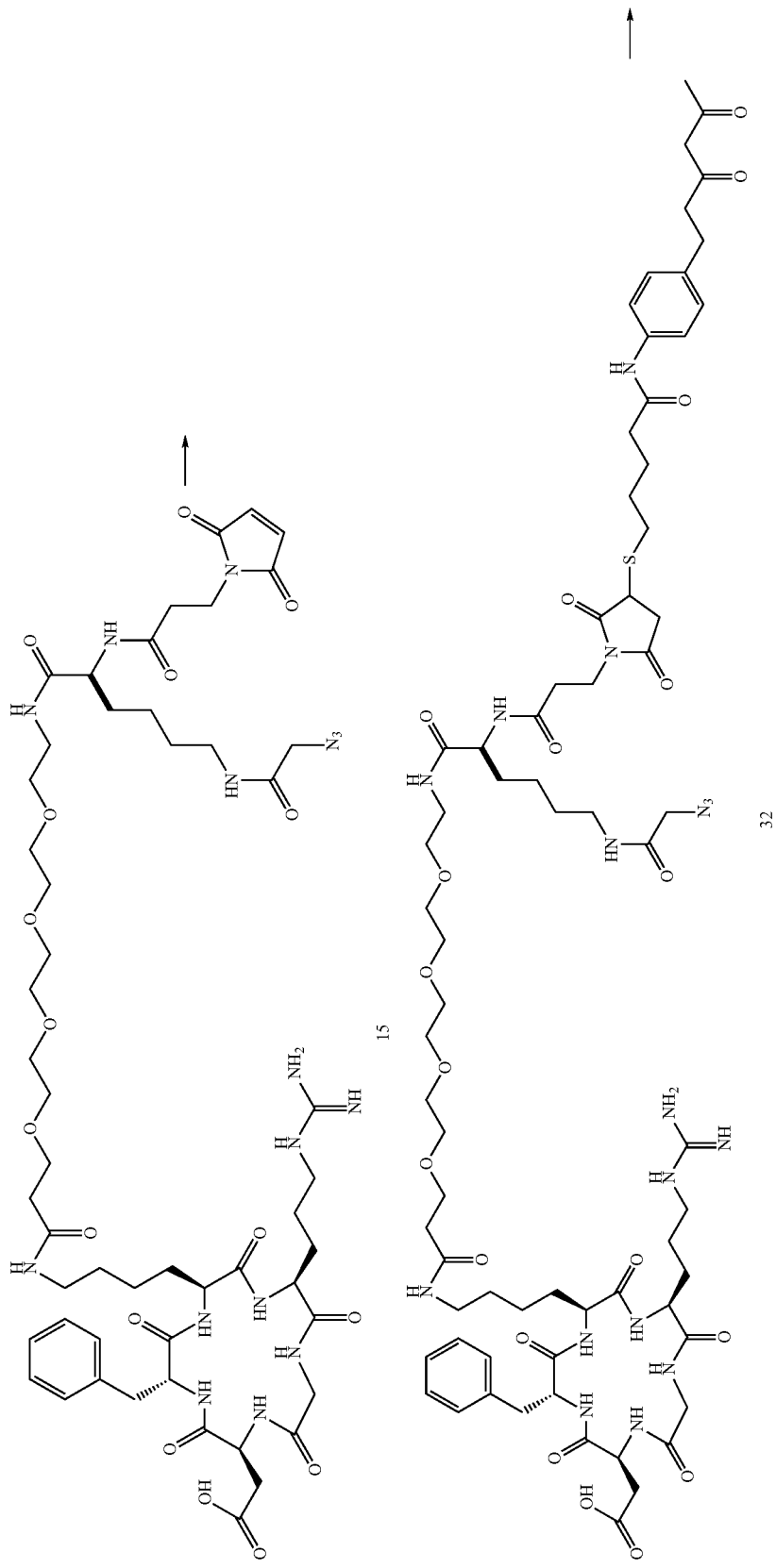

-continued
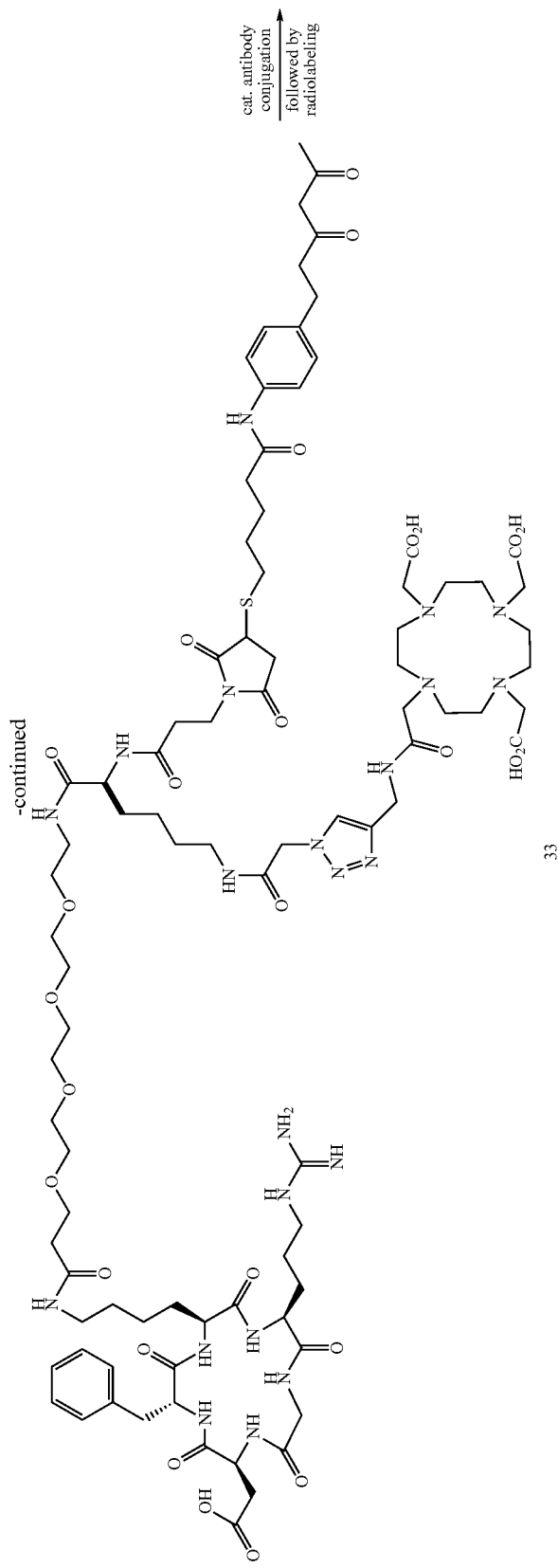
33

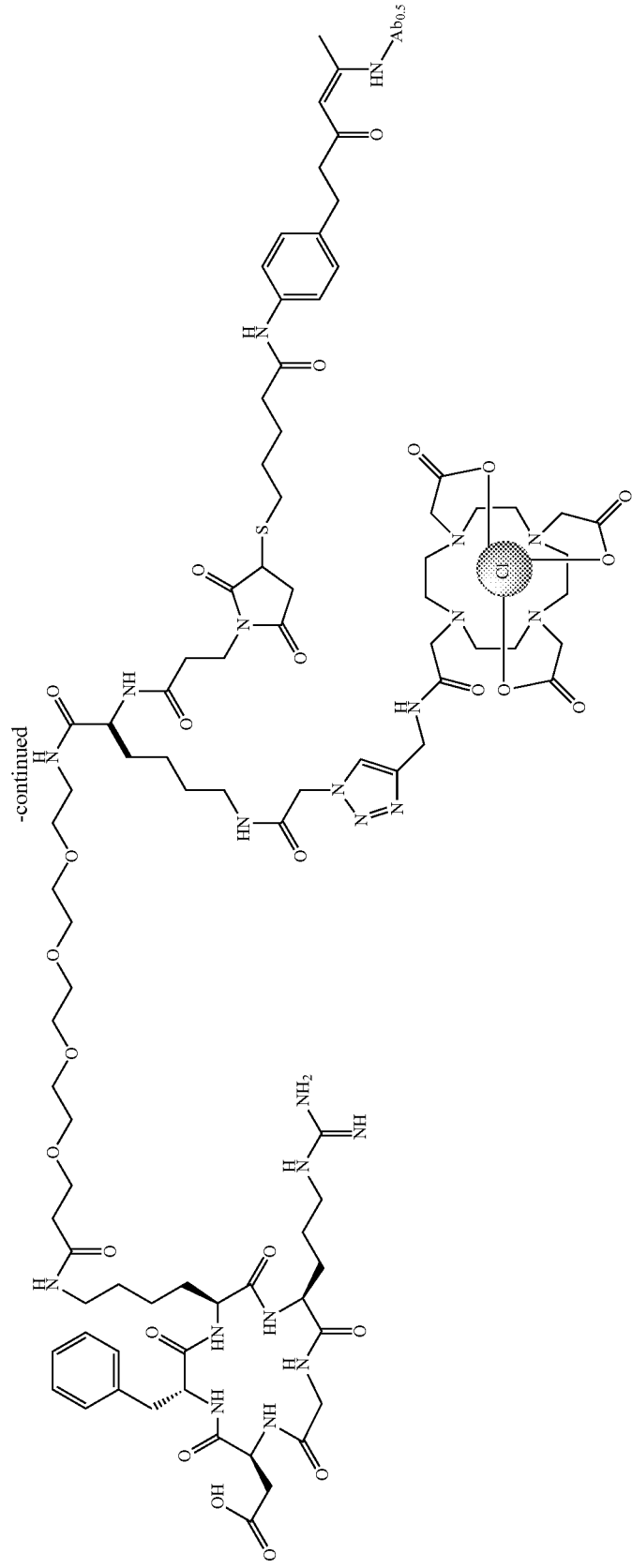

The invention will now be further described by way of the following non-limiting examples.

EXAMPLE 1

Synthesis of a Trifunctional Linker

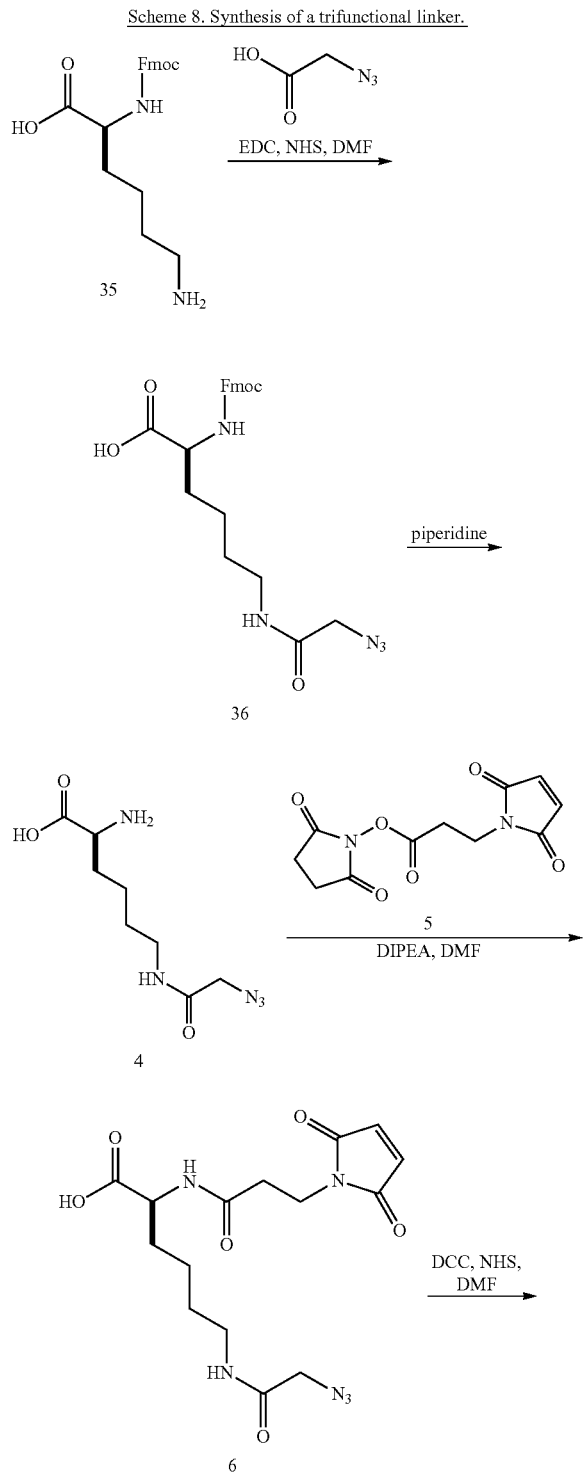

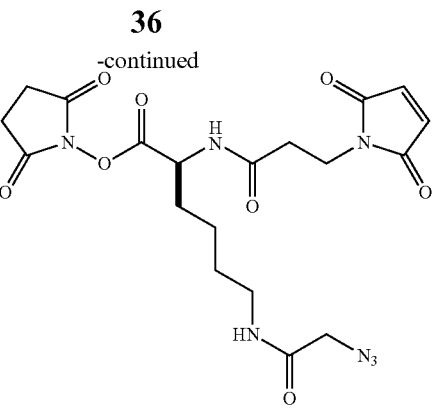

8
Trifunctional Linker

Synthesis of Compound 36:

A round bottom flask containing glycine azido acid (1.6 g, 16.5 mmol, 5% soln in $CH_2Cl_2$) in DMF (3 mL) was treated with EDC (3.2 g, 16.5 mmol) and N-hydroxysuccinimide (NHS) (1.9 g, 16.5 mmol) at rt for 2 hr. To this mixture was added Fmoc-lysine (4.0 g, 10.7 mmol) in DMF (50 mL). The mixture was stirred at rt overnight. The mixture was diluted with water (100 mL), the aq. layer was extracted with EtOAc (3×100 mL). The organic layer was washed with water (2×200 mL), dried ($Na_2SO_4$), filtered and concentrated to dryness. The viscous oil was washed with $Et_2O$ (3×50 mL) and dried in vacuo to afford (4.0 g, 82% yield) of a white foamy solid.

MS (ESI) m/z 452.1 (M+H$^+$).

Synthesis of Compound 4:

To a round bottom flask containing compound 36 (4.0 g, 8.9 mmol) was treated with piperidine (20 mL). The reaction was stirred at rt for 2 hrs. Piperidine was removed in vacuo and the residue was washed with $Et_2O$ (3×50 mL) to afford compound 4 (2.2 g, 100% yield) as a white solid.

MS (ESI) m/z 230.1 (M+H$^+$).

Synthesis of Compound 6:

To a round bottom flask containing compound 4 (0.1 g, 0.44 mmol) in DMF (3 mL) was treated with 2,5-dioxopyrrolidin-1-yl 3-(2,5-dioxo-2,5-dihydro-1H-pyrrol-1-yl)propanoate (5) (0.12 g, 0.44 mmol) followed by DIPEA (0.056 g, 0.44 mmol) and the mixture was stirred at rt for 4 hr. The reaction was deemed complete by LC/MS. The crude product was carried onto the next step without purification.

MS (ESI) m/z 381.1 (M+H$^+$).

Synthesis of the Trifunctional Linker 8:

To a round bottom flask containing crude 6 was added DCC (0.054 g, 0.26 mmol) and NHS (0.03 g, 0.26 mmol) and the reaction was further diluted with DMF (2 mL). The mixture was stirred at rt overnight. The reaction was deemed complete by LC/MS.

MS (ESI) m/z 478.0 (M+H$^+$).

EXAMPLE 2
Synthesis of a "Paint and Destroy" Precursor and Non-Labeled Standard
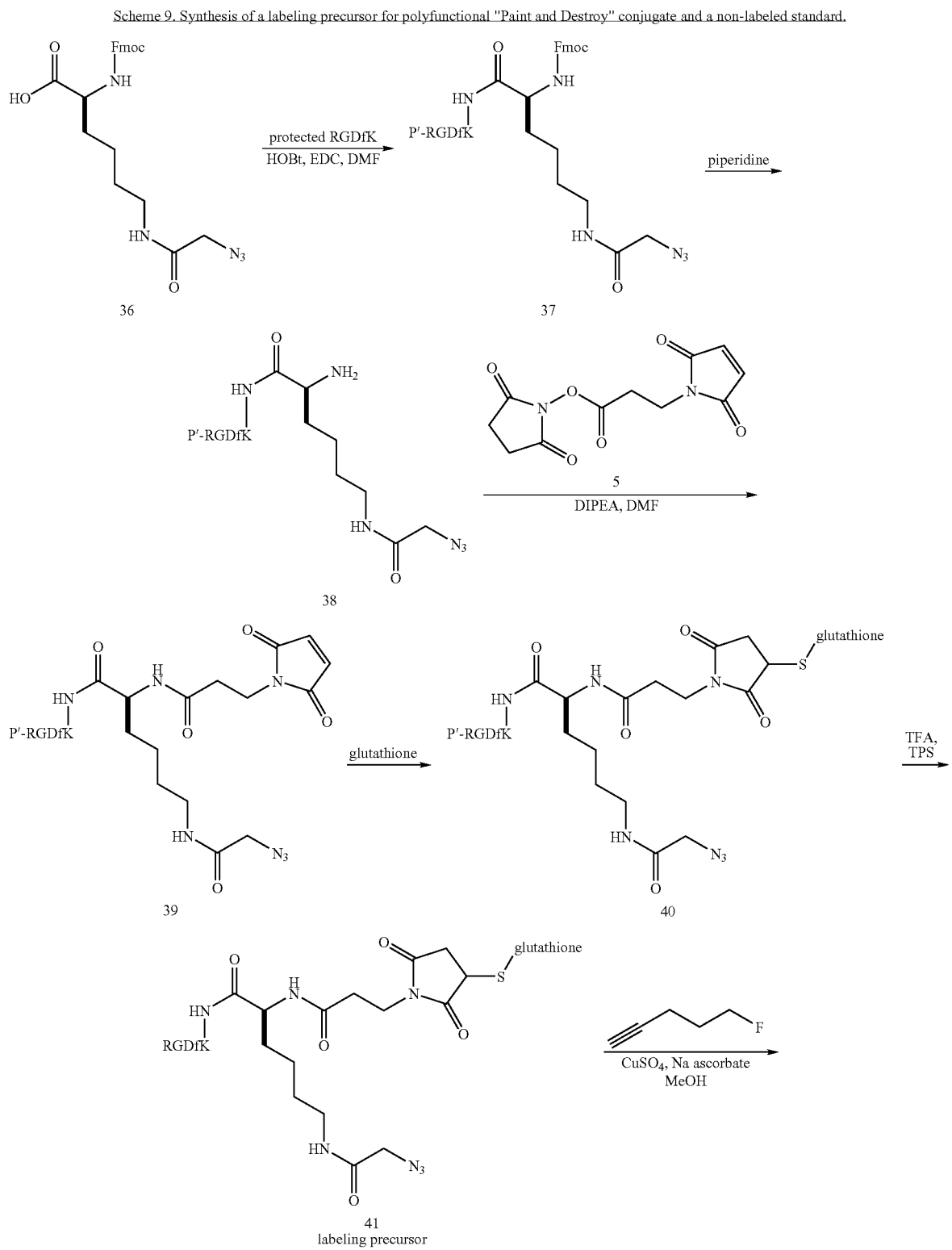
Scheme 9. Synthesis of a labeling precursor for polyfunctional "Paint and Destroy" conjugate and a non-labeled standard.

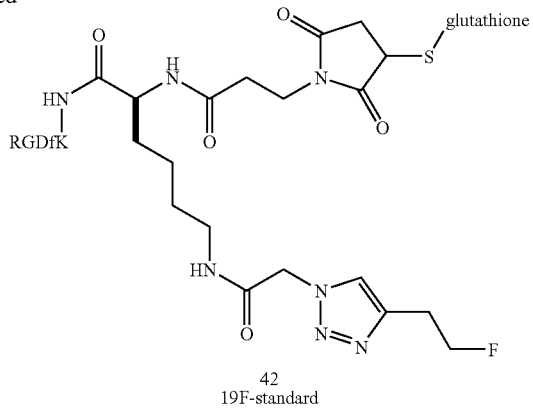

42
19F-standard

Synthesis of Compound 37:

To a round bottom flask containing 36 (127 mg, 0.25 mmol) in DMF (2.5 mL) was added HOBt (34 mg, 0.25 mmol) and EDC (48 mg, 0.25 mmol). The reaction was stirred at rt for 30 min. Commercially available protected RGDfK (t-Boc protected D, Pbf protected R) (200 mg, 0.21 mmol) was added followed by DIPEA (73 uL, 0.42 mmol). The reaction was stirred at RT overnight. The reaction was concentrated in vacuo via co-evaporation with acetonitrile (3×5 mL). The residue was suspended in EtOAc (30 mL), sonicated for 30 min, filtered, washed with EtOAc (2×5 mL), water (2×10 mL) and Et$_2$O (5×5 mL). The resultant white solid was dried under vacuum to afford compound 37 (230 mg, 81% yield) of a white solid. MS (ESI) m/z 1345.5 (M+H$^+$)

Synthesis of Compound 38:

To a round bottom flask containing compound 37 (221 mg) in DCM (4 mL) was added piperidine (0.83 mL) and the reaction was stirred at rt overnight. The mixture was concentrated to dryness via co-evaporation with ACN. The residue was suspended in Ether (15 mL), sonicated (30 min) and filtered. The solid was washed with water (15 mL) and filtered again, followed by drying via lyophilization to afford compound 38 (150 mg, 81% yield). MS (ESI) m/z 1123.5 (M+H$^+$)

Synthesis of Compound 39:

To a round bottom flask containing compound 38 (30 mg, 0.027 mmol) in DMF (0.5 mL) is treated with DIPEA (9.3 uL, 0.053 mmol) and 2,5-dioxopyrrolidin-1-yl 3-(2,5-dioxo-2,5-dihydro-1H-pyrrol-1-yl)propanoate (5) (14 mg, 0.053 mmol), the mixture is stirred at rt for 30 min. The mixture was concentrated in vacuo via co-evaporation with MeCN (2 mL×3). The residue was suspended in diethyl ether (10 mL); the off-yellow precipitate was collected via filtration to afford compound 39 (33 mg, 100% yield). MS (ESI) m/z 1274.5 (M+H$^+$)

Synthesis of Compound 40:

To a round bottom flask containing compound 39 (30 mg, 0.024 mmol) in DMSO (0.1 mL) and THF (0.4 mL) is added glutathione (10.9 mg, 0.035 mmol) in water (0.2 mL). The reaction is stirred at rt for 20 min. The reaction is concentrated in vacuo, washed with water (2 mL×3) and diethyl ether (2 mL×3) and dried in vacuo to afford a white solid compound 40 (24 mg, 65% yield). MS (ESI) m/z 1581.6 (M+H$^+$)

Synthesis of Compound 41:

To a round bottom flask containing 40 (24 mg, 0.015 mmol) is added a mixture of TFA:TPS:water (95:2.5:2.5, 1 mL) and the solution stirred at rt for 4 hr. The reaction is concentrated in vacuo, redissolved in water (5 mL), filtered through a 0.45 micron filter, and purified via RP-HPLC using a gradient of water and ACN both containing 0.05% TFA to afford compound 41 (10 mg, 52% yield) after lyophilization. $^1$H NMR (D$_2$O, 400 MHz), δ: 7.17-7.05 (m, 5H), 4.60 (m, 2H), 4.45 (m, 2H), 4.18 (m, 1H), 4.05 (d, 1H, J=15.2 Hz), 3.95-3.82 (m, 2H), 3.79 (s, 2H), 3.78 (s, 2H), 3.70-3.55 (m, 4H), 3.31 (d, 1H, J=6.0 Hz) 3.20-2.70 (m, 12H), 2.45-2.30 (m, 6H), 2.03-1.96 (m, 2H), 1.72-1.60 (m, 1H), 1.60-1.50 (m, 4H), 1.40-1.25 (m, 5H), 1.22-1.10 (m, 4H), 0.82-0.78 (m, 2H); Mass Spec (lo-res): Calc'd for C$_{52}$H$_{76}$N$_{18}$O$_{18}$S, calc'd: 1272.5, found: 1273.4 (M+H$^+$)

Synthesis of Compound 42:

To a round bottom flasking containing 41 (1 mg, 0.785 umol) in MeOH (0.5 mL) is added CuSO$_4$ (0.2 M in water, 3.9 uL), sodium ascorbate (0.5 M in water, 1.57 uL) and fluoropentyne (3.38 mg, 0.039 mmol). The reaction is stirred at rt for 30 hr. The reaction is concentrated in vacuo, diluted with water (5 mL) and purified via RP-HPLC using a gradient of water and ACN both containing 0.05% TFA to afford compound 42 (1 mg, 94% yield) after lyophilization. $^1$H NMR (D$_2$O, 400 MHz), δ: 7.62 (s, 1H), 7.17-7.05 (m, 5H), 4.98 (s, 2H), 4.60 (m, 2H), 4.45 (m, 3H), 4.25 (m, 1H), 4.15 (m, 1H), 4.05 (d, 1H, J=15.2 Hz), 3.95-3.82 (m, 2H), 3.79 (s, 2H), 3.76 (m, 1H), 3.60-3.55 (m, 3H), 3.31 (d, 1H, J=6.0 Hz) 3.10-2.60 (m, 15H), 2.45-2.30 (m, 6H), 2.03-1.90 (m, 5H), 1.72-1.60 (m, 1H), 1.60-1.50 (m, 4H), 1.40-1.25 (m, 5H), 1.22-1.10 (m, 5H), 0.82-0.78 (m, 2H); $^{19}$F NMR (CDCl$_3$, 376 MHz), δ: −76.14, −219.43 (tt, J=47 Hz, 27 Hz); Mass Spec (lo-res): Calc'd for C$_{57}$H$_{83}$FN$_{18}$O$_{18}$S, calc'd: 1358.6, found: 1359.5 (M+H$^+$)

EXAMPLE 3

Description of 18F-Labeling Process and Process Controls for [F-18]-labeled Targeting Agents ($^{18}$F-TA)

A general discussion of each step follows the flow chart. While the automated synthesis procedure is the method preferred, the entire process can be run manually inside of a shielded isolator using remote handling tools.

A typical labelling sequence is shown below. Briefly, an [F-18] intermediate is prepared and conjugated to an elaborated scaffold to afford the final [F-18]-labeled tracer. In this particular example, the conjugation is effected via click chemistry.

Scheme 10. Exemplary labeling sequence for targeting agents.

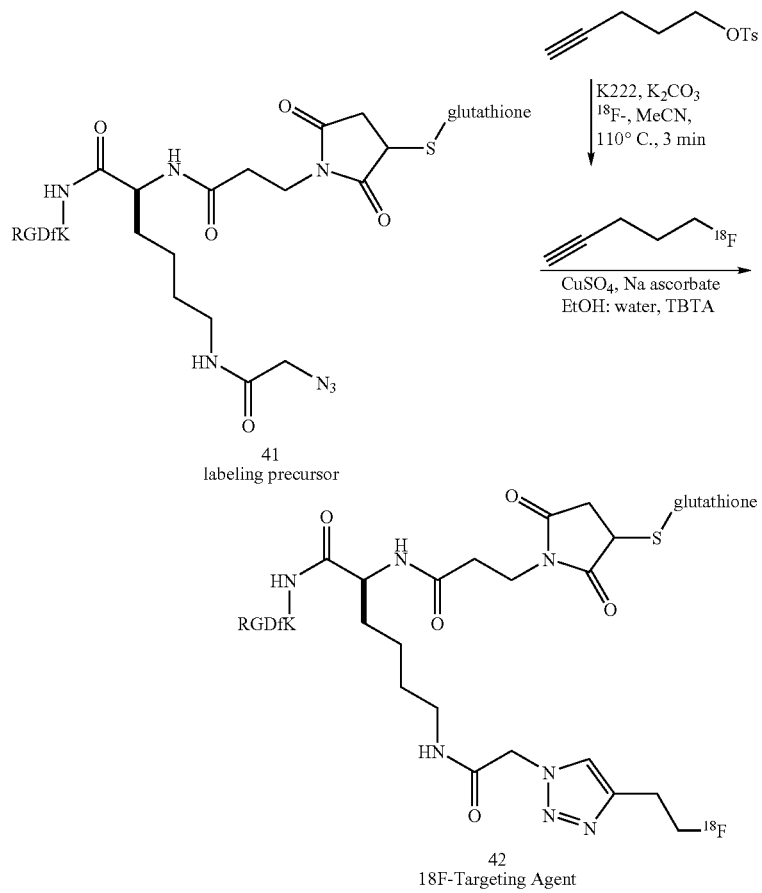

41
labeling precursor 42
18F-Targeting Agent

General [F-18]TA Process Flow Chart

Process for the Production of [F-18] Fluoride Ion

Fluorine-18 [F-18] is produced by proton bombardment of the stable isotope, oxygen-18 (O-18) as illustrated by the reaction scheme as follows:

$^{18}O(p,n)^{18}F$

For bombardment, the chemical form of the enriched O-18 is [O-18]$H_2O$. The [F-18]Fluorine produced is aqueous [F-18] fluoride ion. The target water is loaded into an approximately 1-2 mL target and pressurized to approximately 350 psi. The tantalum target body is outfitted with a high strength, durable metal foil. The foil is an alloy referred to as, "Havar®". The major components of Havar® are cobalt, nickel, chromium, and iron. This thin Havar® foil window permits entry of the protons, yet is sufficiently durable to withstand the pressurized water and proton irradiation. Both targets are made of tantalum metal and are used exclusively for the production of F-18.

After proton bombardment, the [O-18]$H_2O$ containing the [F-18]fluoride ion is transferred to a shielded enclosure ("hot cell"). The aqueous [F-18]Fluoride is then separated from the [O-18]$H_2O$.

Extraction of [F-18]Fluoride and Conversion to Anhydrous Form

Aqueous [F-18]Fluoride ion produced in the cyclotron target, as described in the preceding section, is passed through an anion exchange resin cartridge. The [O-18]$H_2O$ readily passes through the anion exchange resin while [F-18]fluoride is retained. The [F-18]fluoride is eluted from the column using a solution of potassium carbonate (3 mg) in water (0.4 mL) and is collected in a reaction vessel. Kryptofix® 222 (20 mg) dissolved in acetonitrile (1 mL) is added to the aqueous [F-18]fluoride mixture in the reaction vessel. The Kryptofix sequesters the potassium ions preventing the formation of strong $K^+/F$ ion-pairs. This increases the chemical reactivity of the [F-18]fluoride ions.

Alternatively, TBA-$HCO_3$ may be used in place of potassium carbonate and Kryptofix® 222. The use of TBA-$HCO_3$ to generate [F-18]TBAF to perform $^{18}F$-labeling reactions is well known in the art.

The mixture is dried by heating between 70-95° C. under a stream of inert gas and/or reduced pressure (250 mbar) and additional aliquots of acetonitrile may added to insure the fluoride mixture is sufficiently dry for fluorinations. This evaporation step removes the water and converts the [F-18] to an anhydrous form, which is much more reactive than aqueous [F-18]fluoride.

Reaction of Anhydrous [F-18]Fluoride with Pentyne Tosylate

A solution of the tosylate precursor, (20 mg±5 mg, 75 μmol) dissolved in a polar aprotic solvent compatible with $^{18}F$-fluorination such as DMSO, tetrahydrofuran, DMF or MeCN (0.5 mL) is added to the reaction vessel containing the anhydrous [F-18]Fluoride. The vessel is heated to approximately 110±5° C. for 3 minutes to induce displacement of the tosylate leaving group by [F-18]fluoride as illustrated in Scheme 11. The $^{18}$F-fluoropentyne is distilled from the reaction vessel into the mixture containing a click precursor. This distillation may begin as soon as the tosylate is added to the reaction mixture.

Scheme 11. Anhydrous [F-18]Fluoride Displacement Reaction with Pentynyl

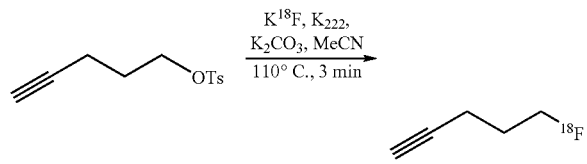

General Coupling of 18F-fluoropentyne with Precursor to Prepare a Labelled [F-18]TA The $^{18}$F-pentyne is distilled into a solution containing the Targeting Agent precursor (TA-precursor) 41 (3.0-4.0 mg) dissolved in 200 uL of EtOH:water 1:1, TBTA (15 mg), sodium ascorbate (40 mg), and 250 µL of 0.1 M CuSO$_4$. The reaction is allowed to react at room temperature for 10-20 min. Prior to purification by HPLC, the reaction is diluted with water (3.5 mL) for loading onto a 4 mL HPLC load loop.

HPLC Purification of [F-18]TA

The reaction mixture containing the crude [F-18]TA (18F-42) is transferred to the HPLC sample loop and purified via chromatographic separation using a semi-preparative HPLC column (Either ACE C18 Pyramid, 7µ, 250×10 mm, Phenomenex Luna, C18, 5µ, 10×250 mm, Phenomenex Gemini C18, 250×10 mm or Phenomenex Synergi Hydro-RP C18, 250×10 mm, using a gradient system, up to 5.5 mL/min, however lower flow rates may be used if there is a high backpressure, or the system may start at a lower flow rate and then increase to the maximum flowrate). The column effluent is monitored using UV (254 or 280 nm) and radiometric detectors connected in series. The purified [F-18]TA tracer is collected from the column at the retention time window determined for the corresponding TA reference standard which coincides with the time that the radiometric detectors begin showing the main peak. The retention time of the [F-18]TA in this system varies between approximately 20-40 minutes.

Gradient:

| Time | % MeCN w/ 0.05% TFA | % H$_2$O w/ 0.05% TFA |
|---|---|---|
| 7 min | 0% | 100% |
| 5 min | 5% | 95% |
| 5 min | 10% | 90% |
| 5 min | 15% | 85% |
| 5 min | 20% | 80% |
| 5-10 min (depending on when the product elutes) | 25% | 75% |
| 10 min (flushes 18F-pentyne from the column) | 95% | 5% |

General Formulation, Sterile Filtration and Aseptic Filling of Purified [F-18]TA The purified [F-18]TA fraction (18F-42) eluted from the HPLC purification column is diluted with water (40-100 mL) and captured onto a C18 SepPak cartridge. The C18 SepPak cartridge is washed with water (10 mL) followed by elution of the product with 0.5-1.0 mL of EtOH. The sample is then diluted with sterile water (4.5-9.0 mL of water) to afford a final formulation of [F-18]TA in a maximum of 10% EtOH: water.

High Pressure Liquid Chromatography (HPLC) Analysis of the Final Product

Mobile phase: A—0.05% TFA in Acetonitrile; B—0.05% TFA in Deionized Water, Flow rate: 1 mL/min Gradient Program:

| Time (minutes) | % A (0.05% TFA in ACN) | % B (0.05% TFA in Water) |
|---|---|---|
| 0 | 5 | 95 |
| 3 | 5 | 95 |
| 15 | 50 | 50 |
| 30 | 95 | 5 |
| 35 | 5 | 95 |

| HPLC System Component | Manufacturer |
|---|---|
| Quaternary Pump | Agilent |
| Injector, Autosampler | Agilent |
| UV Detector | Agilent |
| Radiation Detector | Raytest |
| Column | Phenomenex |
| Data Acquisition System | Raytest |

Labeling Results:

| Tracer | Synthesis time (min) | % Yield (decay corrected) | SA (Ci/umol) | % RCP | Vol (mL) | RT$_{semiprep}$ | RT$_{analytical}$ |
|---|---|---|---|---|---|---|---|
| $^{18}$F-42 | 90 min | 2% | >1.0 | >99% | 10 | 28 | 10.5 |

EXAMPLE 4

PET Imaging Studies

Non-invasive microPET imaging studies were carried out using the U87MG tumor model (human glioblastoma, integrin $\alpha_v\beta_3$ positive) or BXPC3 tumor model (human pancreas adenocarcinoma) under isoflurane anesthesia and capturing either static (30 min scan beginning at 90 min after injection) or dynamic imaging (continuous scan for 120 min). Each mouse received between 100 and 300 uCi of tracer. A baseline scan with $^{18}$F-RGDK5 was performed to show that the tumors were indeed integrin $\alpha_v\beta_3$ positive. A subsequent scan was carried out with $^{18}$F-42 and also showed that the tracer localized favorably at the tumor site with a tumor:muscle ratio of ≧1.5 to 1. The targeting agent, RGD, was successful in localizing glutathione to the tumor site.

FIG. 4 shows the baseline dynamic scan with $^{18}$F-RGD-K5 on a U87MG xenograft tumor.

FIG. 5 shows the static scan with $^{18}$F-RGD-K5 on a BXPC3 xenograft tumor.

FIG. 6 shows the baseline dynamic scan with $^{18}$F-42 on a U87MG xenograft tumor.

FIG. 7 shows the static scan with $^{18}$F-42 on a BXPC3 xenograft tumor.

The invention is further described by the following numbered paragraphs:

1. A polyfunctional compound of the Formula I:

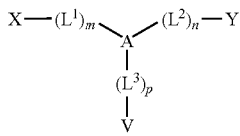

wherein:

A is a low molecular weight scaffold selected from the group consisting of functionalized monocyclic and polycyclic hydrocarbons, functionalized monocyclic and polycyclic heterocycles, an amino acid residue, linear peptides, cyclic peptides, synthetic peptides, semisynthetic peptides, peptidomimetics and hyaluronic acid, and derivatives thereof;

each L1, L2 and L3 is independently a bond, a linker selected from the group consisting of an amino acid residue, —O—, —S—, —S(O)—, —S(O)$_2$—, —NR$^a$—, C$_{1-6}$alkyl, and —(CH$_2$CH$_2$O)$_{1-15}$, wherein R$^a$ is H, C$_{1-5}$alkyl, heterocyclyl, aryl, or heteroaryl, and wherein 1 or 2 carbon atoms of the C$_{1-6}$alkyl are optionally replaced by a —O—, —C(O)—, —C(O)NR'—, —S—, —S(O)—, —S(O)$_2$—, —S(O)$_2$NR'— or —NR'— wherein R' is H or C$_{1-5}$alkyl, and wherein the C$_{1-6}$alkyl is optionally substituted with 1 or 2 substituents selected from the group consisting of —OH, —SH, —NH$_2$, heterocyclyl, aryl and heteroaryl;

V is —N$_3$ or C$_2$-C$_4$alkynyl;

X is an activated moiety of a carboxyl group;

Y is electrophilic group; and each of m, n and p is independently an integer of 1 to 10;

or a pharmaceutically acceptable salt thereof, optionally in the form of a single stereoisomer or mixtures of stereoisomers thereof.

2. The compound of paragraph 1, wherein A is selected from the group consisting of an amino acid residue, linear peptides, cyclic peptides, synthetic peptides, semisynthetic peptides, peptidomimetics and derivatives thereof.

3. The compound of paragraphs 1 or 2, wherein A is an amino acid residue or a dipeptide.

4. The compound of any of paragraphs 1-3, wherein A is a lysine residue.

5. The compound of any of paragraphs 1-4, wherein:

A is selected from the group consisting of an amino acid residue, linear peptides, cyclic peptides, synthetic peptides, semisynthetic peptides, peptidomimetics and derivatives thereof;

each L$^1$, L$^2$ and L$^3$ is independently a bond or a C$_{1-6}$alkyl, wherein 1 or 2 carbon atoms of the C$_{1-6}$alkyl are optionally replaced by a —O—, —C(O)—, —C(O)NR'—, —S—, —S(O)—, —S(O)$_2$—, —S(O)$_2$NR'— or —NR'—, wherein R' is H or C$_{1-5}$alkyl, and wherein the C$_{1-6}$alkyl is optionally substituted with 1 or 2 substituents selected from the group consisting of —OH, —SH, —NH$_2$, heterocyclyl, aryl and heteroaryl; and each of m, n and p is 1.

6. The compound of any of paragraphs 1-6, wherein:

A is selected from the group consisting of functionalized monocyclic and polycyclic hydrocarbons, functionalized monocyclic and polycyclic heterocycles, an amino acid residue, linear peptides, cyclic peptides, synthetic peptides, semisynthetic peptides, peptidomimetics and hyaluronic acid, and derivatives thereof;

each L$^1$, L$^2$ and L$^3$ is independently a bond or a C$_{1-6}$alkyl, wherein 1 or 2 carbon atoms of the C$_{1-6}$alkyl optionally replaced by a —O—, —C(O)—, —C(O)NR'—, —S—, —S(O)—, —S(O)$_2$—, —S(O)$_2$NR'— or —NR'—, wherein R' is H or C$_{1-5}$alkyl, and wherein the C$_{1-6}$alkyl is optionally substituted with 1 or 2 substituents selected from the group consisting of —OH, —SH, —NH$_2$, heterocyclyl, aryl and heteroaryl;

X is 1-oxypyrrolidine-2,5-dione or 1-oxycarbonyl-2,5-dione;

Y is maleimidyl or —C(O)CH$_2$CH$_2$-maleimidyl; and each of m, n and p is 1.

7. A compound of the formula II

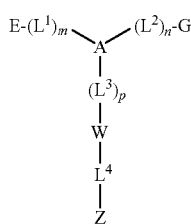

wherein:

A is a low molecular weight scaffold selected from the group consisting of functionalized monocyclic and polycyclic hydrocarbons, functionalized monocyclic and polycyclic heterocycles, an amino acid residue, linear peptides, cyclic peptides, synthetic peptides, semisynthetic peptides, peptidomimetics and hyaluronic acid, and derivatives thereof;

each L$^1$, L$^2$, L$^3$ and L$^4$ is independently a bond, a linker selected from the group consisting of an amino acid residue, —O—, —S—, —S(O)—, —S(O)$_2$—, —NR—, C$_{1-6}$alkyl, and —(CH$_2$CH$_2$O)$_{1-15}$, wherein R$^a$ is H or C$_{1-5}$alkyl, heterocyclyl, aryl, or heteroaryl, and wherein 1 or 2 carbon atoms of the C$_{1-6}$alkyl are optionally replaced by a —O—, —C(O)—, —C(O)NR'—, —S—, —S(O)—, —S(O)$_2$—, —S(O)$_2$NR'— or —NR'—, wherein R' is H or C$_{1-5}$alkyl, and wherein the C$_{1-6}$alkyl is optionally substituted with 1 or 2 substituents selected from the group consisting of —OH, —SH, —NH$_2$, heterocyclyl, aryl and heteroaryl;

E is a targeting agent;

G is a chemotherapeutic agent or an antibody;

W is a triazole;

Z is a moiety comprising a non-radioactive element, a radionuclide selected from the group consisting of positron or gamma emitter, or a chelator of a positron or gamma emitter, said chelator optionally chelated to a positron or gamma emitter; and each of m, n and p is independently an integer of 1 to 10;

or a pharmaceutically acceptable salt thereof, optionally in the form of a single stereoisomer or mixtures of stereoisomers thereof.

8. The compound of paragraph 7, wherein A is selected from the group consisting of an amino acid residue, linear peptides, cyclic peptides, synthetic peptides, semisynthetic peptides, peptidomimetics and derivatives thereof.

9. The compound of paragraphs 7 or 8, wherein A is an amino acid residue or a dipeptide.

10. The compound of any of paragraphs 7-9, wherein A is a lysine residue.

11. The compound of any of paragraphs 7-10, wherein:
A is selected from the group consisting of an amino acid residue, linear peptides, cyclic peptides, synthetic peptides, semisynthetic peptides, peptidomimetics and derivatives thereof;
  each $L^1$, $L^2$, $L^3$ and $L^4$ is independently a bond or a $C_{1-6}$alkyl,
  wherein 1 or 2 carbon atoms of the $C_{1-6}$alkyl are optionally replaced by a —O—, —C(O)—, —C(O)NR'—, —S—, —S(O)—, —S(O)$_2$—, —S(O)$_2$NR'— or —NR'—, wherein R' is H or $C_{1-5}$alkyl, and wherein the $C_{1-6}$alkyl is optionally substituted with 1 or 2 substituents selected from the group consisting of —OH, —SH, —NH$_2$, heterocyclyl, aryl and heteroaryl; and
  each of m, n and p is 1.

12. The compound of any of paragraphs 7-11, wherein:
A is selected from the group consisting of functionalized monocyclic and polycyclic hydrocarbons, functionalized monocyclic and polycyclic heterocycles, an amino acid residue, linear peptides, cyclic peptides, synthetic peptides, semisynthetic peptides, peptidomimetics and hyaluronic acid, and derivatives thereof;
  each $L^1$, $L^2$ and $L^3$ is independently a bond or a $C_{1-6}$alkyl wherein 1 or 2 carbon atoms of the $C_{1-6}$alkyl are optionally replaced by a —O—, —C(O)—, —C(O)NR'—, —S—, —S(O)—, —S(O)$_2$—, —S(O)$_2$NR'— or —NR'—, wherein R' is H or $C_{1-5}$alkyl, and
  wherein the $C_{1-6}$alkyl is optionally substituted with 1 or 2 substituents selected from the group consisting of —OH, —SH, —NH$_2$, heterocyclyl, aryl and heteroaryl;
  $L^4$ is a $C_{1-6}$alkyl wherein 1 or 2 carbon atoms of the $C_{1-6}$alkyl are optionally replaced by a —O—, —C(O)—, —C(O)NR'—, —S—, —S(O)—, —S(O)$_2$—, —S(O)$_2$NR'— or —NR'—, wherein R' is H or $C_{1-5}$alkyl, and
  wherein the $C_{1-6}$alkyl is optionally substituted with 1 or 2 substituents selected from the group consisting of —OH, —SH, —NH$_2$, heterocyclyl, aryl and heteroaryl;
  E is an RGD derivative or a CA-IX ligand;
  G is a chemotherapeutic agent or an antibody;
  W is a triazole; and
  Z comprises a non-radioactive element, a radionuclide selected from the group consisting of positron or gamma emitter or a chelator of a positron or gamma emitter, said chelator optionally chelated to a positron or gamma emitter; and
  each of m, n and p is 1.

13. The compound of any of paragraphs 7-12, wherein the chemotherapeutic agent is selected from the group consisting of doxorubicin, cyclophosphamide, vincristine, streptozotocin, bevacizumab, prednisone and paclitaxel.

14. The compound of any of paragraphs 7-13, wherein the antibody is a catalytic antibody.

15. The compound of any of paragraphs 7-14, wherein the catalytic antibody converts a prodrug into an active drug.

16. The compound of any of paragraphs 7-15, wherein the non-radioactive element is selected from the group consisting of F, I and Br, and the radionuclide is selected from the group consisting of $^{11}$C, $^{13}$N, $^{15}$O, $^{18}$F, $^{61}$Cu, $^{62}$Cu, $^{64}$Cu, $^{67}$Cu, $^{68}$Ga, $^{124}$I, $^{125}$I, $^{131}$I, $^{99}$Tc, $^{75}$Br, $^{153}$Gd and $^{32}$P.

17. The compound of any of paragraphs 7-16, wherein the radionuclide is selected from the group consisting of $^{11}$C, $^{18}$F, $^{125}$I and $^{64}$Cu.

18. A compound comprising any one of the formulae:

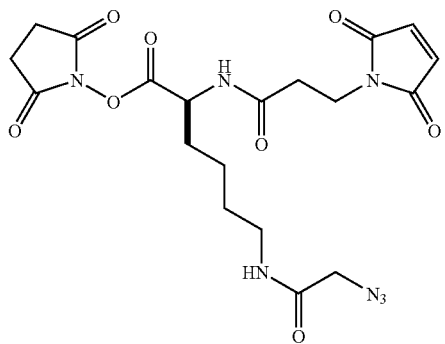

8

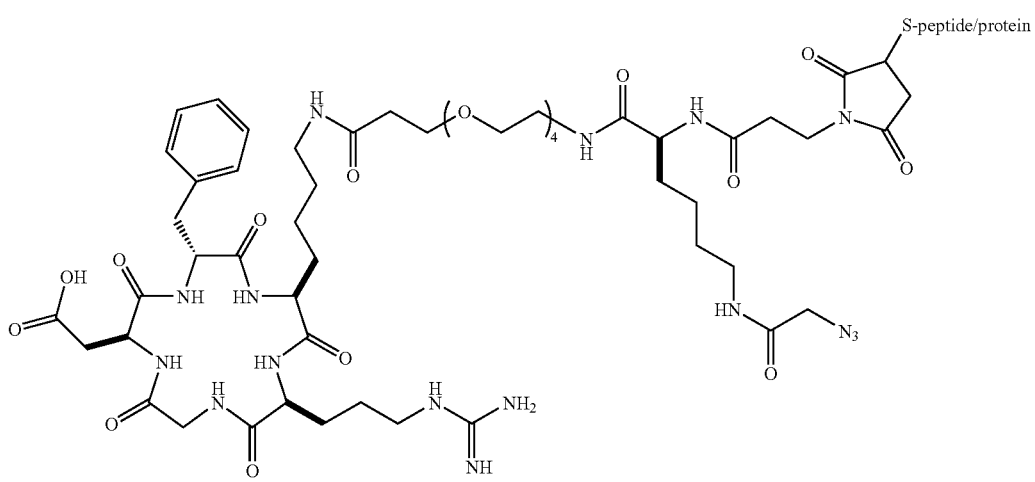

16

-continued
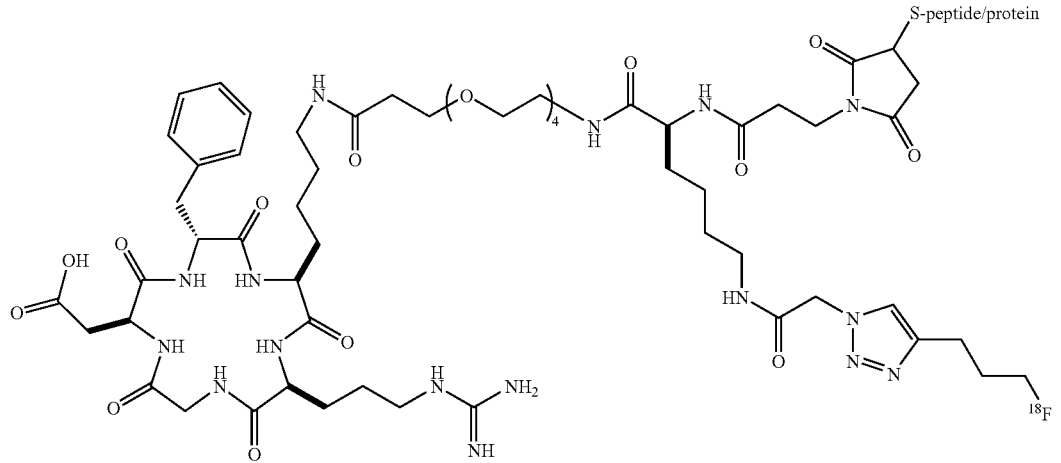
17
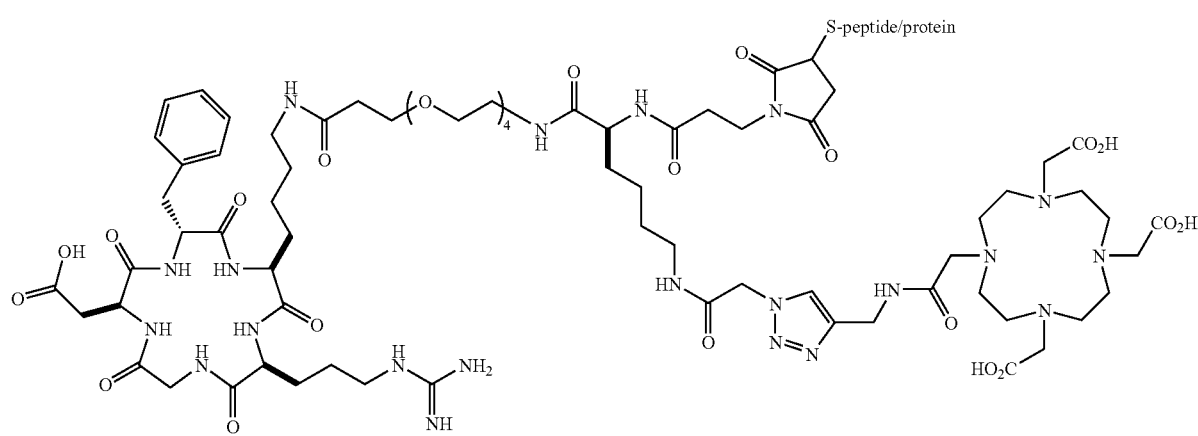
30
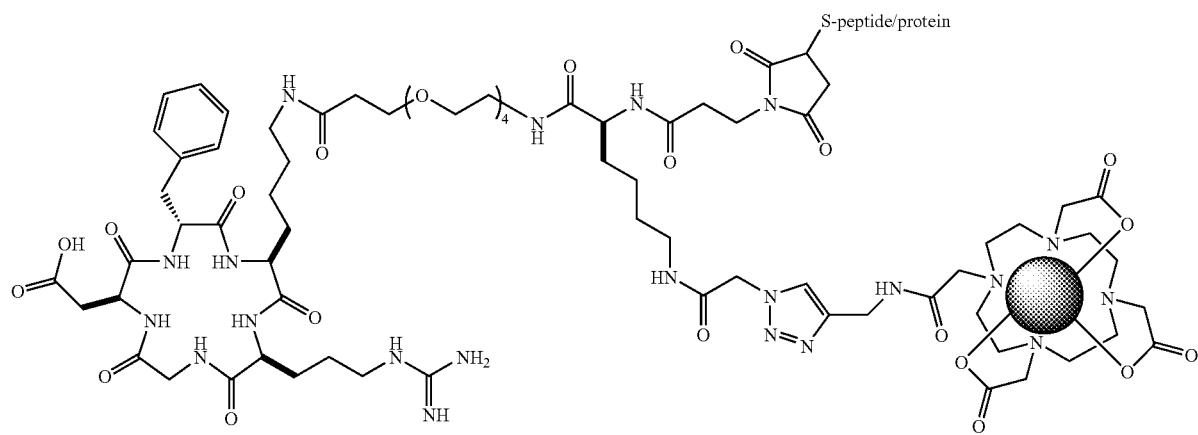
31

-continued

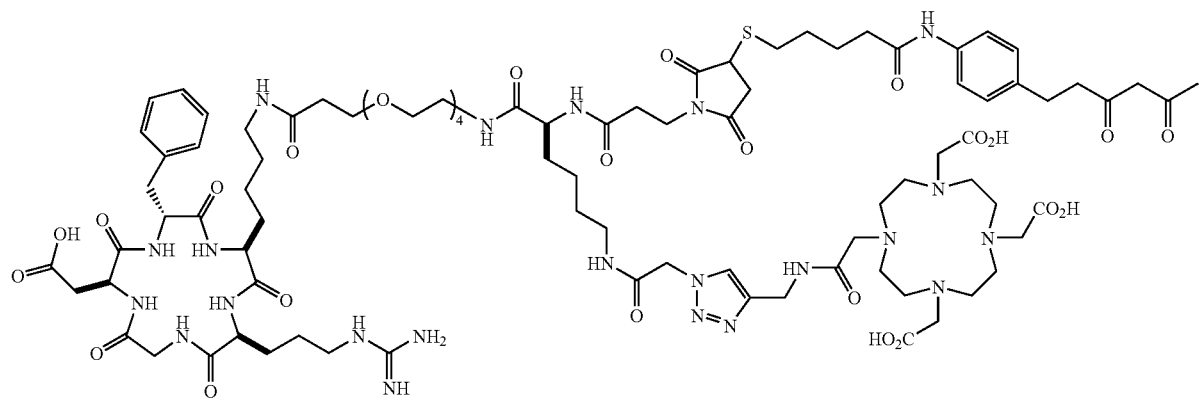

33

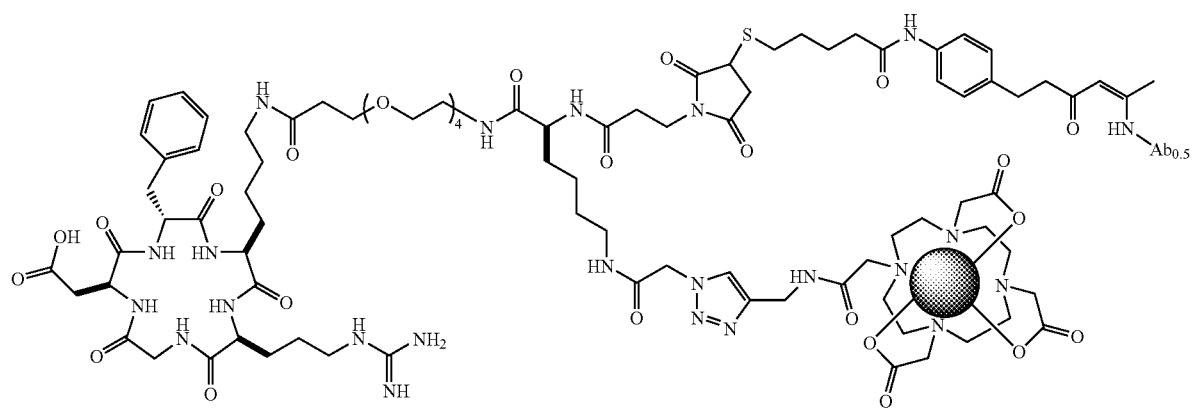

34

19. A pharmaceutical composition comprising a therapeutically effective amount of a compound of any one of paragraphs 7-18, and a pharmaceutically acceptable excipient, optionally in the form of a single stereoisomer or mixture of stereoisomers thereof.

20. A method for treating cancer in a patient in need of such treatment, the method comprising:
a) prequalifying a patient's therapeutic treatment by performing a molecular imaging procedure to the patient using a labeled biomarker specific for a cancer target at the tumor site; and
b) administering a therapeutic effective amount of a compound of any one of paragraphs 7-18 or a pharmaceutical composition of paragraph 19, comprising a targeting agent linked to a chemotherapeutic or a targeting agent linked to an antibody.

21. The method of paragraph 20, wherein the molecular imaging procedure is positron emission tomography (PET).

22. The method of paragraphs 20 or 21, wherein the therapeutically effective amount is effective to treat cancer.

\* \* \*

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed:
1. A polyfunctional compound of the Formula I:

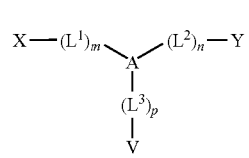

wherein:
A is a low molecular weight scaffold being at least one member of the group consisting of: functionalized monocyclic and polycyclic hydrocarbons, functionalized monocyclic and polycyclic heterocycles, an amino acid residue, linear peptides, cyclic peptides, synthetic peptides, semisynthetic peptides, peptidomimetics and hyaluronic acid, and derivatives thereof;
each $L^1$, $L^2$ and $L^3$ is independently a bond, or a linker being at least one member of the group consisting of: an amino acid residue, —O—, —S—, —S(O)—, —S(O)$_2$—, —NR$^a$—, $C_{1-6}$alkyl, (CH$_2$CH$_2$O)$_{1-15}$, wherein R$^a$ is at least one member of the group consisting of: H, $C_{1-5}$alkyl, heterocyclyl, aryl, or heteroaryl, and wherein 1 or 2 carbon atoms of the $C_{1-6}$alkyl is replaced by at least one of —O—, —C(O)—, —C(O)NR'—, —S—, —S(O)—, —S(O)$_2$—, —S(O)$_2$NR'— or —NR'— where R' is H or $C_{1-5}$alkyl, and where the $C_{1-6}$alkyl is optionally substituted with 1 or 2 substituents selected from the group consisting of —OH, —SH, —NH$_2$, heterocyclyl, aryl and heteroaryl;

V is —N$_3$ or C$_2$-C$_4$alkynyl;

X is an activated moiety of a carboxyl group;

Y is an electrophilic group; and each m, n and p is independently an integer of 1 to 10;

or a pharmaceutically acceptable salt thereof, optionally in the form of a single stereoisomer or mixtures of stereoisomers thereof.

2. The compound of claim 1, wherein A is selected from the group consisting of an amino acid residue, linear peptides, cyclic peptides, synthetic peptides, semisynthetic peptides, peptidomimetics and derivatives thereof.

3. The compound of claim 1, wherein A is an amino acid residue or a dipeptide.

4. The compound of claim 3, wherein A is a lysine residue.

5. The compound of claim 1, wherein:

A is selected from the group consisting of an amino acid residue, linear peptides, cyclic peptides, synthetic peptides, semisynthetic peptides, peptidomimetics and derivatives thereof;

each L$^1$, L$^2$ and L$^3$ is independently a bond or a C$_{1-6}$alkyl wherein 1 or 2 carbon atoms of the C$_{1-6}$alkyl is replaced by a —O—, —C(O)—, —C(O)NR'—, —S—, —S(O)—, —S(O)$_2$—, —S(O)$_2$NR'— or —NR'— wherein R' is H or C$_{1-5}$alkyl, and wherein the C$_{1-6}$alkyl is optionally substituted with 1 or 2 substituents selected from the group consisting of —OH, —SH, —NH$_2$, heterocyclyl, aryl and heteroaryl; and each m, n and p is 1.

6. The compound of claim 1, wherein:

A is selected from the group consisting of functionalized monocyclic and polycyclic hydrocarbons, functionalized monocyclic and polycyclic heterocycles, an amino acid residue, linear peptides, cyclic peptides, synthetic peptides, semisynthetic peptides, peptidomimetics and hyaluronic acid, and derivatives thereof;

each L$^1$, L$^2$ and L$^3$ is independently a bond or a C$_{1-6}$alkyl wherein 1 or 2 carbon atoms of the C$_{1-6}$alkyl is replaced by a —O—, —C(O)—, C(O)NR'—, —S—, —S(O)—, —S(O)$_2$—, —S(O)$_2$NR'— or —NR'— wherein R' is H or C$_{1-5}$alkyl, and wherein the C$_{1-6}$alkyl is optionally substituted with 1 or 2 substituents selected from the group consisting of —OH, —SH, —NH$_2$, heterocyclyl, aryl and heteroaryl;

X is 1-oxypyrrolidine-2,5-dione or 1-oxycarbonyl-2,5-dione;

Y is maleimidyl or —C(O)CH$_2$CH$_2$-maleimidyl; and each m, n and p is 1.

7. The compound of claim 1, wherein the compound is selected from the group consisting of:

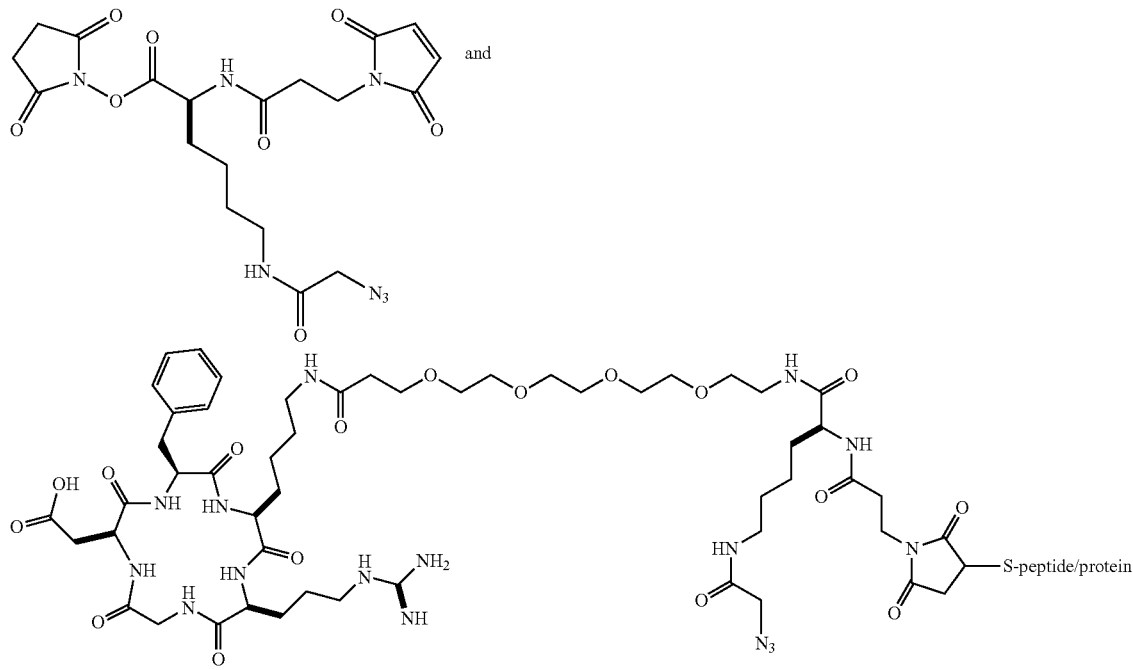

and

8. A compound of Formula Ia:

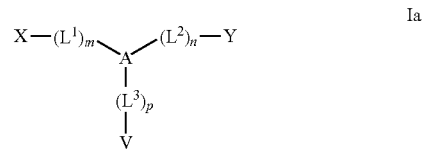

wherein:

A is a low molecular weight scaffold being at least one member of the group consisting of: functionalized monocyclic and polycyclic hydrocarbons, functionalized monocyclic and polycyclic heterocycles, an amino acid residue, linear peptides, cyclic peptides, synthetic peptides, semisynthetic peptides, peptidomimetics and hyaluronic acid, and derivatives thereof, each L$^1$, L$^2$ and L$^3$ is independently a bond, or a linker being at least one member of the group consisting of: an amino acid residue, —O—, —S—, —S(O)—, —S(O)$_2$—, —NR$^a$—, C$_{1-6}$alkyl, (CH$_2$CH$_2$O)$_{1-15}$, wherein R$^a$ is at least one member of the group consisting of: H, C$_{1-5}$alkyl, heterocyclyl, aryl, or heteroaryl, and
wherein 1 or 2 carbon atoms of the C$_{1-6}$alkyl is replaced by at least one of: —O—, —C(O)—, —C(O)NR'—, —S—, —S(O)—, —S(O)$_2$—, —S(O)$_2$NR'— or —NR'— where R' is H or C$_{1-5}$alkyl, and where the C$_{1-6}$alkyl is optionally substituted with 1 or 2 substituents selected from the group consisting of —OH, —SH, —NH$_2$, heterocyclyl, aryl and heteroaryl;
V is a radio-labeling site;
X is a targeting agent attachment site;
Y is a peptide conjugation site; and
each m, n and p is independently an integer of 1 to 10;
or a pharmaceutically acceptable salt thereof, optionally in the form of a single stereoisomer or mixtures of stereoisomers thereof.

9. The compound of claim 8, wherein the radiolabeling site comprises:

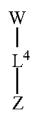

wherein:
W is a triazole;
L$^4$ is independently a bond, a linker selected from the group consisting of an amino acid residue, —O—, —S—, —S(O)—, —S(O)$_2$—, —NR$^a$—, C$_{1-6}$alkyl and (CH$_2$CH$_2$O)$_{1-15}$; and
Z is a moiety comprising a non-radioactive element, a radionuclide selected from the group consisting of positron or gamma emitter or a chelator of a positron or gamma emitter, said chelator optionally chelated to a positron or gamma emitter.

10. The compound of claim 8, wherein X comprises an RGD derivative or a CA-IX ligand.
11. The compound of claim 1, wherein X and Y are each maleimidyl.
12. The compound of claim 1, wherein V is an alkyne.
13. The compound of claim 1, wherein A is hyaluronic acid and derivatives thereof.
14. The compound of claim 1, wherein A is a linear peptide and derivatives thereof.
15. The compound of claim 1, wherein the compound is:

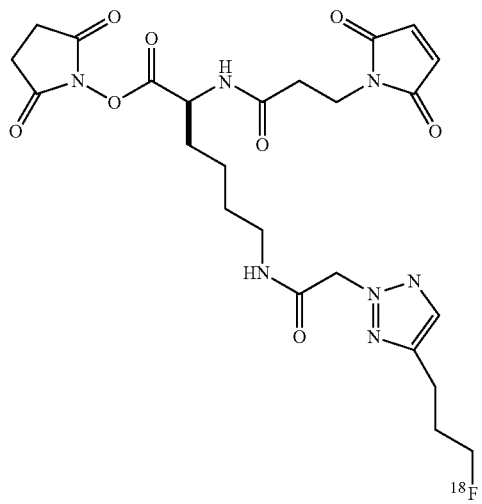

16. The compound of claim 9, wherein Z is a radionuclide.
17. The compound of claim 9, wherein Z is a chelator of a positron or gamma emitter.
18. The compound of claim 9, wherein X is an RGD derivative or a CA-IX ligand.
19. The compound of claim 18, wherein Y is maleimidyl.
20. A compound of Formula I:

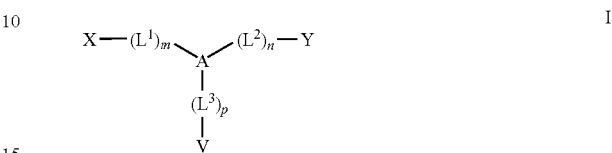

wherein:
A is at least one of a lysine or a derivative thereof;
each L$^1$, L$^2$ and L$^3$ is independently a bond, or a linker being at least one member of the group consisting of: an amino acid residue, —O—, —S—, —S(O)—, —S(O)$_2$—, —NR$^a$—, C$_{1-6}$alkyl, (CH$_2$CH$_2$O)$_{1-15}$,
wherein R$^a$ is at least one member of the group consisting of: H, C$_{1-5}$alkyl, heterocyclyl, aryl, or heteroaryl, and
wherein 1 or 2 carbon atoms of the C$_{1-6}$alkyl is replaced by at least one of —O—, —C(O)—, —C(O)NR'—, —S—, —S(O)—, —S(O)$_2$—, —S(O)$_2$NR'— or —NR'— where R' is H or C$_{1-5}$alkyl, and where the C$_{1-6}$alkyl is optionally substituted with 1 or 2 substituents selected from the group consisting of —OH, —SH, —NH$_2$, heterocyclyl, aryl and heteroaryl;
V is an azide or C$_2$-C$_4$alkynyl;
X is an activated moiety of a carboxyl group;
Y is an electrophilic group; and
each m, n and p is independently an integer of 1 to 10;
or a pharmaceutically acceptable salt thereof; optionally in the form of a single stereoisomer or mixtures of stereoisomers thereof.

21. The compound of claim 20, wherein Y is maleimidyl.
22. The compound of claim 20, wherein A is a derivative of lysine.
23. The compound of claim 20, wherein L$^3$ is C$_{1-6}$alkyl, wherein 1 or 2 carbon atoms of the C$_{1-6}$alkyl is replaced by at least one of: —O—, —C(O)—, —C(O)NR'—, —S—, —S(O)—, —S(O)$_2$—, —S(O)$_2$NR'— or —NR'— where R' is H or C$_{1-5}$alkyl, and where the C$_{1-6}$alkyl is optionally substituted with 1 or 2 substituents selected from the group consisting of —OH, —SH, —NH$_2$, heterocyclyl, aryl and heteroaryl.
24. The compound of claim 21, wherein X is maleimidyl.
25. The compound of claim 20, wherein the compound is:

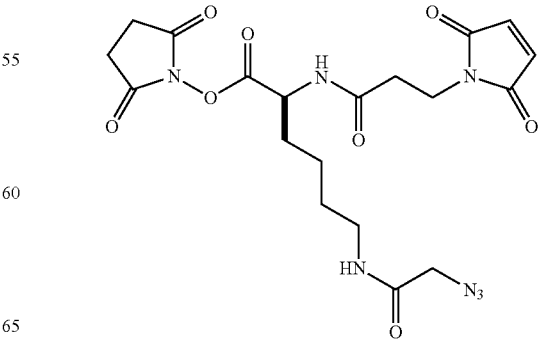

26. A compound of Formula I:

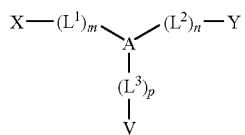

wherein:
A is at least one of a lysine or a derivative thereof;
each $L^1$, $L^2$ and $L^3$ is independently a bond, or a linker being at least one member of the group consisting of: an amino acid residue, —O—, —S—, —S(O)—, —S(O)$_2$—, —NR$^a$—, $C_{1-6}$alkyl, (CH$_2$CH$_2$O)$_{1-15}$,
wherein R$^a$ is at least one member of the group consisting of: H, $C_{1-5}$alkyl, heterocyclyl, aryl, or heteroaryl, and
wherein 1 or 2 carbon atoms of the $C_{1-6}$alkyl is replaced by at least one of: —O—, —C(O)—, —C(O)NR'—, —S—, —S(O)—, —S(O)$_2$—, —S(O)$_2$NR'— or —NR'— where R' is H or $C_{1-5}$alkyl, and where the $C_{1-6}$alkyl is optionally substituted with 1 or 2 substituents selected from the group consisting of —OH, —SH, —NH$_2$, heterocyclyl, aryl and heteroaryl;
V is an azide or $C_2$-$C_4$alkynyl;
X is an RGD derivative;
Y is an electrophilic group; and
each m, n and p is independently an integer of 1 to 10;
or a pharmaceutically acceptable salt thereof, optionally in the form of a single stereoisomer or mixtures of stereoisomers thereof.

27. A compound of Formula Ia:

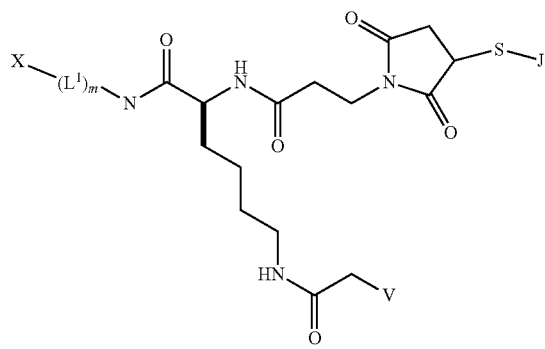

wherein:
$L^1$ is independently a bond, or a linker being at least one member of the group consisting of:
an amino acid residue, —O—, —S—, —S(O)—, —S(O)$_2$—, —NR$^a$—, $C_{1-6}$alkyl, (CH$_2$CH$_2$O)$_{1-15}$
wherein R$^a$ is at least one member of the group consisting of: H, $C_{1-5}$alkyl, heterocyclyl, aryl, or heteroaryl, and
wherein 1 or 2 carbon atoms of the $C_{1-6}$alkyl is replaced by at least one of: —O—, —C(O)—, —C(O)NR'—, —S—, —S(O)—, —S(O)$_2$—, —S(O)$_2$NR'— or —NR'— where R' is H or $C_{1-5}$alkyl, and where the $C_{1-6}$alkyl is optionally substituted with 1 or 2 substituents selected from the group consisting of —OH, —SH, —NH$_2$, heterocyclyl, aryl and heteroaryl;
J is at least one member of the group consisting of: a peptide and a protein;
V is a radio-labeling site;
X is at least one member of the group consisting of: an activated moiety of a carboxyl group and a targeting agent attachment site;
each m, n and p is independently an integer of 1 to 10;
or a pharmaceutically acceptable salt thereof, optionally in the form of a single stereoisomer or mixtures of stereoisomers thereof.

28. The compound of claim 27, wherein V comprises:

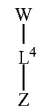

wherein:
W is a triazole;
$L^4$ is independently a bond, a linker selected from the group consisting of an amino acid residue, —O—, —S—, —S(O)—, —S(O)$_2$—, —NR$^a$—, $C_{1-6}$alkyl and (CH$_2$CH$_2$O)$_{1-15}$; and
Z is a moiety comprising a non-radioactive element, a radionuclide selected from the group consisting of positron or gamma emitter or a chelator of a positron or gamma emitter, said chelator optionally chelated to a positron or gamma emitter.

29. The compound of claim 27, wherein $L^1$ is a linker of (CH$_2$CH$_2$O)$_{1-15}$.

30. The compound of claim 27, wherein X is a targeting agent attachment site.

* * * * *